United States Patent [19]

Shih et al.

[11] Patent Number: 5,786,358

[45] Date of Patent: Jul. 28, 1998

[54] PYRIDOPYRIMIDINES AS NONCLASSICAL ANTIFOLATES

[75] Inventors: Chuan Shih, Carmel; Lynn S. Gossett; William J. Gill, both of Indianapolis, all of Ind.; Edward C. Taylor, Princeton, N.J.; James T. Metz, Indianapolis, Ind.

[73] Assignee: The Trustees of Princeton University, Princeton, N.J.

[21] Appl. No.: 708,351

[22] Filed: Sep. 4, 1996

Related U.S. Application Data

[60] Provisional application No. 60/003,471 Sep. 8, 1995.

[51] Int. Cl.[6] ............... C07D 471/02; A61K 31/505
[52] U.S. Cl. ............................ 514/258; 544/279
[58] Field of Search ................. 544/279; 514/258

[56] References Cited

U.S. PATENT DOCUMENTS

| | | | |
|---|---|---|---|
| 4,684,653 | 8/1987 | Taylor et al. | 514/258 |
| 4,818,819 | 4/1989 | Taylor et al. | 544/279 |
| 4,889,859 | 12/1989 | Taylor et al. | 514/258 |
| 4,895,946 | 1/1990 | Taylor et al. | 544/279 |
| 5,008,391 | 4/1991 | Barnett et al. | 546/243 |
| 5,144,012 | 9/1992 | Johnson et al. | 530/391.9 |
| 5,159,079 | 10/1992 | Pearce et al. | 546/14 |

FOREIGN PATENT DOCUMENTS

| | | |
|---|---|---|
| 91304757 | 5/1991 | European Pat. Off. |
| 07082174-A | 3/1995 | Japan . |

OTHER PUBLICATIONS

Bisset et al., "Quinazoline Antifolates Inhibiting Thymidylate Synthase: Synthesis and Biological Activity of γ-Linked Peptide and Amide Analogues of 2-Desamino-2-Methyl-N10-Propargyl-5,8,-Dideazafolic Acid (ICI 198583)", Tenth International Symposium, Chemistry and Biology of Pteridines and Folates, Orange Beach, Alabama, Final Program and Abstract Book, p. 135 (Mar. 21–26, 1993).

Habeck et al., "A Novel Class of Monoglutamated Antifolates Exhibits Tight-binding Inhibiton of Human Glycinamide Ribonucleotide Formyltransferase and Potent Activity against Solid Tumors", Cancer Research, 54, pp. 1021–1026 (Feb. 15, 1994).

Howbert et al., "Novel Agents Effective against Solic Tumors: The Diarylsulfonylureas. Synthesis, Activities, and Analysis of Quantitative Structure–Activity Relationships", J. Med. Chem., 33:9, pp. 2393–2407 (1990).

Kaminski, "2–Chloro–4,6–dimethoxy–1,3,5–triazine. A New Coupling Reagent for Peptide Synthesis", Communications, pp. 917–920 (1987).

Rosowsky et al., "Methotrexate Analogues. 20. Replacement of Glutamate by Longer–Chain Amino Diacids: Effects on Dihydrofolate Reductase Inhibition, Cytotoxicity, and in Vivo Antitumor Activity", J. Med. Chem., 36:13, pp. 1719–1724 (1983).

Rosowsky et al., "Side Chain Modified 5–Deazafolate and 5–Deazatetrahydrofolate Analogues as Mammalian Folypolyglutamate Synthetase and Glycinamide Ribonucleotide Formyltransferase Inhibitors: Synthesis and in Vitro Biological Evaluation", J. Med. Chem., 35:9, pp. 1578–1588 (1992).

Singh et al., "Synthesis and Biological Evaluation of N$^{\alpha}$–(5–Deaza–5,6,7,8–tetrahydropteroyl)–L–ornithine", J. Med. Chem., 35:11, pp. 2002–2006 (1992).

Stephens et al., "Use of Murine L5178Y Lynphome Thymidine Kinase (TK) Mutants for In Vitro and In Vivo Antitumour Efficacy Evaluation of Novel Thymidylate Synthase (TS) Inhibitors", Tenth International Symposium, Chemistry and Biology of Pteridines and Folates, Orange Beach, Alabama, Final Program and Abstract Book, p. 134 (Mar. 21–26, 1993).

*Primary Examiner*—Mukund J. Shah
*Assistant Examiner*—Brenda Coleman
*Attorney, Agent, or Firm*—Mathews, Collins, Shepherd & Gould, P.A.

[57] ABSTRACT

2-Amino-4-hydroxy-4,5,6,7-tetrahydropyrido[2,3-d] pyrimidine derivatives of aromatic amides, such as a benzamide or thienylcarboxamide in which the amino portion of the amide is other than L-glutamic acid are inhibitors of enzymes which utilize folic acid, in particular glycinamide ribonucleotide formyl transferase. A typical embodiment is N-(N-{4-[2-(2-amino-4-hydroxy-5,6,7,8-tetrahydropyrido [2,3-d]pyrimidin-6-yl)ethyl]benzoyl}-L-γ-glutamyl)-D-aspartic acid.

32 Claims, No Drawings

PYRIDOPYRIMIDINES AS NONCLASSICAL ANTIFOLATES

CROSS-REFERENCE TO RELATED APPLICATIONS

The benefit of U.S. Provisional Patent Application No. 60/003,471 filed on Sep. 8, 1995 and entitled "NONCLASSICAL ANTIFOLATES" is claimed.

BACKGROUND OF THE INVENTION

Folic acid is used by a number of cells in the course of cell replication. Antifolate compounds mimic folic acid and its derived cofactors, interacting with one or more folate-requiring enzymes. Antifolate compounds inhibit the growth of malignant cells and find use in the treatment of cancer.

Known antifolate compounds, such as Lometrexol (U.S. Pat. Nos. 5,008,391), include a glutamic acid portion in the natural or "L" configuration which undergoes polyglutamation upon entry into a cell by the enzyme polyglutamate synthetase (FPGS). The polyglutamated antifolate then can react with other folate-requiring enzymes such as dihydrofolate reductase (DHFR) and glycinamide ribonucleotide formyl transferase (GARFT), the latter being the first of two folate-dependent enzymes in the de novo purine biosynthetic pathway. Inhibition of DEFR and GARFT and other folate-utilizing enzymes eventually leads to inhibition of cell replication.

The efficacy of classical antifolates in inhibiting cell replication can decrease with continued use. One possible explanation for this is the fact that malignant cells become resistant toward classical antifolates through impaired polyglutamation reactions. As a polyglutamated antifolate reacts more efficiently with folate-requiring enzymes than a monoglutamated antifolate, this lack of polyglutamation could be sufficient to account for the decline in efficacy.

One way of increasing efficacy, in terms of inhibiting cell replication, is to provide an antifolate that does not contain a terminal L-glutamic acid group, thus avoiding the reaction with FPGS. The difficulty in providing such a compound is that in order to be effective in inhibiting cell replication, the compound must still be able to react with other folate requiring enzymes even though it is not polyglutamated.

Use of a non-polyglutamatable inhibitor has been suggested as an approach to the design of DHFR inhibitors targeted against FPGS deficient tumors. See Rosowsky et al., *J. Med. Chem.*, (1983), 26, 1719–1724. In addition, several derivatives of folic acid in which the terminal L-glutamate moiety is replaced by L-ornithine have been shown to be effective FPGS inhibitors. Singh, et al., *J. Med. Chem.*, (1992), 35 (11), 2002–6. Non-polyglutamatable GARFT inhibitors also have been described. Rosowsky, et al., *J. Med. Chem.*, (1992), 35 (9), 1578–88.

DETAILED DESCRIPTION

The present invention pertains to compounds of the formula:

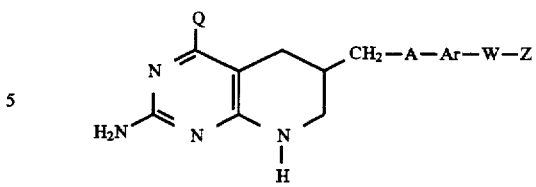

in which:

Q is —OH or —$NH_2$;

A is —$CH_2$—, —$CH_2CH_2$—, —O—, or —S—;

—Ar— is a divalent aromatic ring;

W is —CO— or —$SO_2$—; and

Z is:

(A) an α-amino acid group of the formula

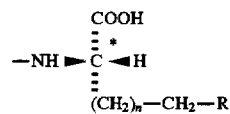

wherein * designates a chiral center in the L configuration, n has a value of from 0 to 4, and R is:

(i) —COJ wherein J is an amino acid linked through the α-amino group, which if chiral, is of the D configuration, (ii) V, wherein V is a tetrazolyl group of the formula

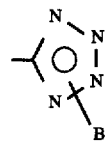

where B is hydrogen, $C_1$–$C_4$ alkyl, or $C_1$–$C_4$ hydroxyalkyl, or (iii) —$SO_3H$;

(B) a tetrazolyl group of the formula

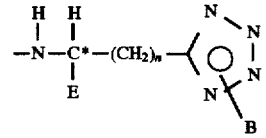

wherein n has a value of from 0 to 4 and E is —COOH or V, wherein V is a tetrazolyl group as defined previously and, if n is greater than 0 or E is other than V, the carbon atom designated * is in the L configuration;

(C) —$NHR^1$, where $R^1$ is hydrogen, —$CH_2$—COOH, or a substituted or unsubstituted $C_1$–$C_4$ alkyl, $C_1$–$C_4$ hydroxyalkyl, cycloalkyl, or polycycloalkyl group;

(D) —$NR^2R^3$ where $R^2$ and $R^3$ are independently $C_1$–$C_4$ alkyl, $C_1$–$C_4$ hydroxyalkyl or COOT, where T is hydrogen or $C_1$–$C_4$ alkyl;

(E)

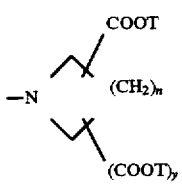

where each T is independently as defined previously, n has a value of from 0 to 4, and y has a value of 0 or 1;

(F)

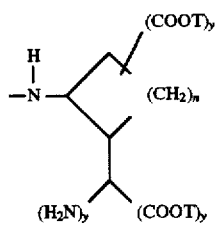

where n, T and y are as defined previously, provided at least one y is other than zero;

(G)

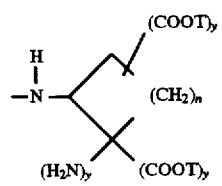

where n, T and y are as defined previously, provided at least one y is other than zero; or (H) —NHOH;

and the pharmaceutically acceptable salts and esters thereof.

The present invention also relates to pharmaceutical compositions containing one or more of the above compounds.

The compounds of Formula I are named herein as derivatives of the pyrido[2,3-d]-pyrimidine fused ring system which is numbered as follows:

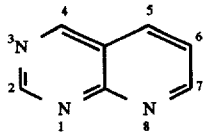

It will be appreciated that the pyrido[2,3-d]pyrimidines of Formula I are the tautomeric equivalent of the corresponding 3-H-4-oxo or 3-H-4-imino structures. For simplicity's sake, the compounds are depicted herein as 4-hydroxy and 4-amino compounds, it being understood the corresponding and tautomeric keto and imino structures, respectively, are fully equivalent; e.g.:

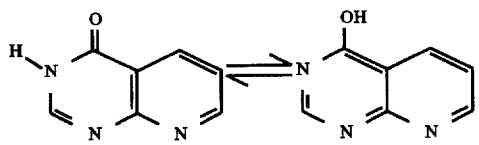

The carbon atom in the 6-position of the 5,6,7,8-tetrahydropyrido[2,3-d]pyrimidine ring is a chiral center leading to two isomers. If a further chiral center is present in Z, this will result in two diastereomers. The mixture of isomers can be utilized therapeutically, both serving as substrates for relevant folate enzymes, or can be separated so as to be in a form substantially free of the other; i.e., in a form having an optical purity of >95%.

The isomers can be separated mechanically, as by chromatography, or the racemate or mixture of diastereomers can be treated with a chiral acid operable form a salt therewith. The resultant diastereoisomeric salts are then separated through one or more fractional crystallization and thereafter the free base of the cationic moiety of at least one of the separated salts is liberated through treatment with a base and removal of the protecting groups. The liberation of the cation of the salt can be performed as a discrete step before or after the removal of the protecting groups or concomitantly with the removal of such groups under basic hydrolysis. Suitable chiral acids include the individual enantiomers of 10-camphorsulfonic acid, camphoric acid, α-bromocamphoric acid, menthoxyacetic acid, tartaric acid, diacetyltartaric acid, malic acid, pyrrolidine-5-carboxylic acid, and the like.

The group-Ar— is a 5- or 6-membered aromatic ring which optionally can contain up to three N, O, or S heteroatoms such as, for example, 1,4-phenylene, 1,3-phenylene, thiene-2,5-diyl, thiene-2,4-diyl, furan-2,4-diyl, and furan-2,5-diyl. Such divalent aromatic rings optionally can be substituted with from 1 to 4 substituents such as bromo, chloro, fluoro, iodo, hydroxy, or $C_1$–$C_4$ alkyl.

"$C_1$–$C_4$ alkyl" includes methyl, ethyl, propyl, isopropyl, n-butyl, isobutyl, sec-butyl and tert.-butyl. "Cycloalkyl" refers to $C_3$–$C_7$ cycloalkyl, such as cyclopropyl, cyclobutyl, cyclopentyl, cyclohexyl, and cycloheptyl. The term "polycycloalkyl" refers to two or more rings, each independently containing from 3 to 15 carbon atoms which share two or more carbon atoms, such as bicyclo[2.2.1]heptane (e.g., norbornane), bicyclo[2.2.2]octa-2-ene, and tricyclo[2.2.1.0$^{2,6}$]heptane (e.g., nortricyclene).

"Amino protecting group" refers to substituents on an amino group commonly employed to protect the amino functionality during one or more reactions. Examples include the formyl, trityl, phthalimido, pivaloyl, trichloroacetyl, chloroacetyl, bromoacetyl, iodoacetyl, benzoylmethylsulfonyl, 2-nitrophenylsulfenyl, and diphenylphosphine oxide group. The protecting group employed is not critical provided the group is stable to the condition of subsequent reactions involving other positions and can be removed at the appropriate point without disrupting the remainder of the molecule. Examples of amino protecting groups can be found in J. W. Barton, "Protective Groups in Organic Chemistry", J. G. W. McOmie, Ed., Plenum Press, New York, N.Y., 1973, Chapter 2; and T. W. Greene, P. G. M. Wuts, "Protective Groups in Organic Synthesis-2nd Edition", John Wiley and Sons, New York, N.Y., 1991, Chapter 7.

"Carboxylic acid protecting group" similarly refers to derivatives of a carboxylic acid group commonly employed to protect a carboxylic acid group. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, methyl, ethyl, propyl, isopropyl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di-(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like. The protecting group employed again is not critical provided the derivatized carboxylic acid is stable to the conditions of the reactions and can be removed at the appropriate point without disrupting the remainder of the molecule. Examples of such groups are found in Barton, "Protective Groups in Organic Chemistry", supra, Chapter 5, and Greene, "Protective Groups in Organic Synthesis, 2nd Edition", supra, Chapter 5.

The compounds of Formula I can form salts with bases and acids. For final usage these are pharmaceutically acceptable salts, although for synthetic steps the salts do not necessarily have to be pharmaceutically acceptable. Examples of salts with acids include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, etc. Preferred pharmaceutically acceptable acid addition salts are those of hydrochloric acid, hydrobromic acid, maleic acid, and methanesulfonic acid.

The present invention also pertains to the physiologically acceptable salts of the fore-going compounds with alkali metals, alkaline earth metals, ammonia and organic amines as, for example, salts in which the cations are sodium, potassium, magnesium, calcium, or the protonated amines such as those derived from ethylamine, triethylamine, ethanolamine, diethylaminoethanol, ethylenediamine, piperidine, morpholine, 2-piperidinoethanol, benzylamine, procaine, etc.

The compound of the present invention generally can be prepared by coupling an amino compound contributing Z with substituted aromatic acids, e.g., benzoic acid and thienyl carboxylic acid intermediates (W=—CO—) or the corresponding sulfonic acid derivatives in which W is —SO$_2$—. These acids are substituted with a 2-amino-4-hydroxy-4,5,6,7-tetrahydropyrido[2,3-d]pyrimidin-6-yl substituent. The coupling reaction is conducted using conventional condensation techniques for forming peptide bonds such as, for example, the use of dicyclohexylcarbodiimide, diphenylchlorophosphonate, or 2-chloro-4,6-dimethoxy-1,3,5-triazine {see, e.g, Kaminski, Synthesis, 917–920 (1987)}, following which any remaining protecting groups are removed.

The benzoic acid and thienyl carboxylic acid intermediates carrying a 2-(2-amino-4-hydroxy-4,5,6,7-tetrahydropyrido[2,3-d]pyrimidin-6-yl)ethyl substituent; i.e., A is —CH$_2$—, can be prepared for example using the procedures of U.S. Pat. No. 4,818,819, the disclosure of which is incorporated herein by reference. This 6-ethynylpyrido[2,3-d]pyrimidine is allowed to react with a compound of the formula X-Ar-COR$^5$ in which X is bromo or iodo and R$^5$ is a carboxy protecting group in the presence of a palladium catalyst. The palladium catalysts are those which have been employed in the reaction of aryl halides and allylic alcohols, as described for example by Melpoler et al., J. Org. Chem., 41 (2), 265 (1976); Chalk et al., J. Org. Chem., 41 (7), 1206 (1976); Arai et al., J. Heterocyclic Chem., 15, 351 (1978); Tamaru et al., Tetrahedron Letters, 10, 919 (1978); and Tetrahedron, 35, 329 (1979); and Sakamoto, Synthesis, (1983) 312. Particularly useful are palladium acetate or a palladium or cuprous halide such as palladium chloride and a cuprous iodide.

The reaction generally is conducted in the presence of at least one molar equivalent of a secondary or tertiary amine which acts as an acid acceptor, as for example triethylamine or diethylamine, and under an inert atmosphere, optionally in the presence of an inert polar solvent such as acetonitrile, dimethylformamide, or N-methylpyrrolidinone. Acetonitrile serves as a solvent for the reactants and for the salt formed from the acid acceptor and acid generated. Moderately elevated temperatures, as for example from about 75° to 125° C., preferably from about 75° to 100° C., generally are employed.

The coupling reaction with the palladium catalyst is followed by catalytic hydrogenation of the carbon-carbon triple bond and the pyridine ring of the pyrido[2,3-d] pyrimidine ring system. Suitable catalysts for this hydrogenation include platinum oxide or palladium-on-carbon. The hydrogenation reaction generally is run at room temperature for approximately 3 to 4 hours, though up to 24 hours may be required for certain compounds in which —Ar— is thienediyl.

The benzoic acid and thienyl carboxylic acid intermediates carrying a 2-amino-4-hydroxy-4,5,6,7-tetrahydropyrido [2,3-d]pyrimidin-6-ylmethoxy or 2-amino-4-hydroxy-4,5,6, 7-tetrahydropyrido[2,3-d]pyrimidin-6-ylmethylthio substituent; ie., A is —O— or —S—, respectively, can be prepared using the procedures of U.S. Pat. No. 5,159,079, the disclosure of which is incorporated by reference, e.g., allowing a 2-amino-4-hydroxy-6-hydroxymethyl-4,5,6,7-tetrahydropyrido[2,3-d]pyrimidine to react with an ester of benzoic acid or thienyl carboxylic acid which is substituted with hydroxy or mercaptan, optionally in the presence of diethyl azodicarboxylate, to form the corresponding ether or thioether.

The benzoic acid and thienyl carboxylic acid intermediates carrying a 3-(2-amino-4-hydroxy-4,5,6,7-tetrahydropyrido[2,3-d]pyrimidin-6-yl)prop-1-yl substituent, i.e., A is —CH$_2$CH$_2$—, can be prepared using the procedures of U.S. Pat. No. 4,895,946, the disclosure of which is incorporated by reference, e.g., condensing a 2,4-diaminopyrimidin-6-one with an ester of benzoic acid or thienyl carboxylic acid which is substituted with an activated dialdehyde such as a dinitrile.

According to the foregoing processes, compounds of Formula I in which Z is hydroxy are obtained. When a compound of Formula I in which Q is amino is desired, a compound in which Q is hydroxy can be treated with 1,2,4-triazole and (4-chlorophenyl)dichlorophosphate and the product of this reaction then treated with concentrated ammonia.

Preferred amino acids for J are glycine, D-aspartic acid, D-proline, and D-homocysteic acid.

Tetrazolyls include 1H-tetrazol-5-yl, 2H-tetrazol-5-yl, 1-methyltetrazol-5-yl, 1-ethyltetrazol-5-yl, 1-propyltetrazol-5-yl, 2-ethyltetrazol-5-yl, 2-methyltetrazol-5-yl, 2-propyltetrazol-5-yl, 1-hydroxymethyltetrazol-5-yl, 2-hydroxymethyltetrazol-5-yl, 1-butyltetrazol-5-yl, 2-butyltetrazol-5-yl, 1-(2-hydroxyethyl)-tetrazol-5-yl, 1-(1-hydroxyethyl)tetrazol-5-yl, 2-(2-hydroxyethyl)tetrazol-5-yl, 2-(1-hydroxyethyl)tetrazol-5-yl, 1-(1-hydroxypropyl)-tetrazol-5-yl, 2-(1-hydroxypropyl)tetrazol-5-yl, 1-(2- hydroxypropyl)tetrazol-5-yl, 2-(2-hydroxypropyl)-tetrazol-5-yl, 1-(1-hydroxybutyl)tetrazol-5-yl, 2-(1-hydroxybutyl)tetrazol-5-yl, 1-(2-hydroxybutyl)tetrazol-5-yl, and 2-(2-hydroxybutyl)tetrazol-5-yl.

A preferred subclass pertains to compound of the formula:

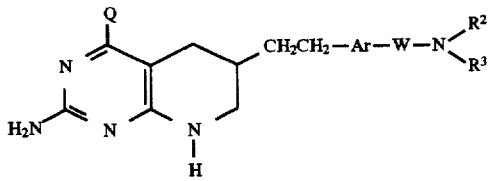

II in which
Ar is phenylene or thienediyl;
W is —CO— or —SO$_2$—;
Q is hydroxy or amino;
(a) $R^2$ and $R^3$ when taken together with the nitrogen atom to which they are attached are a pyrrolidino or piperidino group substituted with one or two groups of the formula COOT in which T is hydrogen or alkyl of 1 to 4 carbon atoms, or
(b) when taken separately, $R^2$ is hydrogen and $R^3$ is:
  (1) hydroxy,
  (2) cycloalkyl of 3 to 8 carbon atoms substituted with —COOT in which T is hydrogen or alkyl of 1 to 4 carbon atoms, or (3) 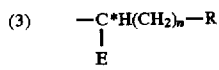

in which
E is hydrogen, carboxy, or tetrazolyl and if E is other than hydrogen the configuration about the carbon atom designated * is L,
n has a value of 0 to 4, and
R is
  (i) —SO$_3$H,
  (ii) glycyl, or
  (iii) —CO—J in which J is an α-amino acid residue of the D-configuration, or when E is not carboxy, hydroxy or alkoxy of 1 to 4 carbon atoms.

Particularly preferred are compounds of Formula II in which Q is hydroxy and W is —CO—.

As noted, the compounds of this invention have an effect on one or more enzymes which utilize folic acid, and in particular metabolic derivatives of folic acid, as a substrate. The compounds are particularly effective inhibitors of GARFT enzyme. For example, N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-aspartic acid demonstrates 100% inhibition against growth of 6C3HED lymphosarcoma tumor evaluated in C3H female mice at 100 mg/kg. The compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides, psoriasis, and arthritis.

The compounds can be administered orally but preferably are administered parenterally, alone or in combination with other therapeutic agents including other anti-neoplastic agents, steroids, etc., to an animal in need of treatment. Animals include mammals, reptiles, crustacean, amphibians, fish, and poultry. The principal target recipient are mammals, particularly humans. Parenteral routes of administration include intramuscular, intrathecal, intravenous and intra-arterial. Dosage regimens must be titrated to the particular neoplasm, the condition of the patient, and the response but generally doses will be from about 10 to about 100 mg/day for 5–10 days or single daily administration of 250–500 mg, repeated periodically; e.g., every 14 days. While having a low toxicity as compared to other antimetabolites now in use, a toxic response often can be eliminated by either or both of reducing the daily dosage or administering the compound on alternative days or at longer intervals such as every three days.

Oral dosage forms including tablets and capsules, contain from 1 to 100 mg of drug per unit dosage. Isotonic saline solutions containing 1–100 mg/mL can be used for parenteral administration. Accordingly, the present invention also includes pharmaceutical compositions comprising as active ingredient one or more compounds of Formula I associated with at least one pharmaceutically acceptable carrier, diluent or excipient.

In preparing compositions containing one or more other compounds of Formula I, the active ingredients are usually mixed with an excipient, diluted by an excipient or enclosed within such a carrier which can be in the form of a capsule or sachet. When the excipient serves as a diluent, it may be a solid, semi-solid or liquid material which acts as a vehicle, carrier or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions can be formulated so as to provide immediate, sustained or delayed release of the active ingredient after administration to the patient by employing known procedures. The compositions are preferably formulated in a unit dosage form. The term "unit dosage form" refers to physically discrete units suitable as unitary dosages for human subjects and other mammals, each unit containing (i) a predetermined quantity of active material calculated to produce, upon administration in a single or multiple dose regimen, the desired therapeutic effect, in association with (ii) a suitable pharmaceutical excipient. However, it will be understood that the amount of the compound actually administered, and the frequency of administration, will be determined by a physician in light of the relevant circumstances including the relative severity of a disease state, the choice of compound to be administered, the age, weight, and response of the individual patient, and the chosen route of administration.

The following examples illustrate specific aspects of the present invention but are not intended to limit the scope thereof in any respect and should not be so construed.

EXAMPLE 1

N-(N-{4-[2-(2-Amino-4-hydroxy-5,6,7,8-tetrahydropyrido[2,3-d]pyrimidin-6-yl)ethyl]benzoyl}-L-γ-glutamyl)-D-aspartic Acid A. To a solution of 1.79 g (5.31 mmol) of N-carbobenzyloxy-L-glutamic acid α-tert.-butyl ester in 25 mL of methylene chloride in a dried, three-necked, 100 mL round bottom flask cooled in an ice bath was added under nitrogen 0.74 mL (5.3 mmol) of triethylamine. The reaction mixture was stirred at 0° C. for ten minutes and 0.69 mL (5.31 mmol) of isobutyl chloroformate was added. The reaction mixture was stirred for 35 minutes and 1.06 g (5.36 mmol) of D-aspartic acid dimethyl ester hydrochloride was added. An additional 0.75 mL (5.3 mmol) of triethylamine was added and the reaction mixture warmed slowly to room temperature overnight, diluted with 80 mL methylene chloride, and washed sequentially with 5% sodium bicarbonate, 0.5N hydrochloric acid, and brine. The organic layer was dried over sodium sulfate and concentrated in vacuo. The product was then chromatographed on silica gel (55% hexanes/ethyl acetate) to give 1.93 g (75%) of dimethyl N-[4-(benzyloxycarbonylamino)-4-tert.-butoxycarbonylbutanoyl]-D-aspartate as a clear viscous oil. Mass Spectrum (FD+): M+1=481; IR (CHCl$_3$, cm$^{-1}$)=1029, 1052, 1155, 1227, 1295, 1348, 1370, 1394, 1408, 1440, 1455, 1508, 1675, 1729, 2957, 2983, 3011, 3428; UV (ethanol) $\lambda_{max}$=201 ($\epsilon$=9875); Anal. Calcd. for C$_{23}$H$_{32}$N$_2$O$_9$: C, 57.48; H, 6.71; N, 5.83. Found: C, 57.14; H, 6.79; N, 5.82. $^1$H NMR (300 MHz, CDCl$_3$) $\delta$1.47 (s, 9H), 1.90–1.98 (m, 1H), 2.19–2.37 (m, 3H), 2.83 (dd, J=4.5 Hz and J=17.2 Hz, 1H), 3.04 (dd, J=4.5 Hz and J=17.2 Hz, 1H), 3.70 (s, 3H), 3.76 (s, 3H), 4.27–4.33 (M, 1H), 4.86–4.91 (m, 1H), 5.11 (s, 2H), 5.57 (d, J=7.8 Hz, 1H), 6.81 (d, J=7.7 Hz, 1H), 7.27–7.37 (m, 5H).

B. To a solution of 1.92 g (4.0 mmol) of dimethyl N-[4-(benzyloxycarbonylamino)-4-tert.-butoxycarbonylbutanoyl]-D-aspartate in 15 mL of anhydrous methanol was added 0.43 g of 10% Pd/C and the mixture was then stirred under an atmosphere of hydrogen overnight. The catalyst was removed by filtration through a Celite® pad and the filtrate concentrated in vacuo to yield 1.45 g of dimethyl N-(4-amino-4-tert.-butoxycarbonylbutanoyl)-D-aspartate as a thick clear oil. Mass Spectrum (FD+): M+1=347; IR (CHCl$_3$, cm$^{-1}$)=840, 1048, 1155, 1371, 1396, 1440, 1511, 1602, 1672, 1739, 2980, 3428, 3691; $^1$H NMR (30 MHz, CDCl$_3$) $\delta$1.51 (s, 9H), 1.66 (s, 2H), 2.07 (m, 2H), 2.46 (m, 2H), 2.85 (t, J=6.0 Hz, 2H), 3.68 (s, 3H), 3.72 (s, 3H), 3.76 (t, J=6.4 Hz, 1H), 4.78 (t, J=5.7 Hz, 1H), 7.15 (d J=8.0 Hz, 1H).

C. To 0.27 g (0.77 mmol) of 4-[2-(2-amino-4-hydroxy-5,6,7,8-tetrahydropyrido[2,3-d]pyrimidin-6-yl)ethyl]benzoic acid hydrochloride in a three-necked round bottomed flask under an atmosphere of nitrogen were added 4.5 mL of anhydrous dimethylformamide and 0.19 mL (1.72 mmol) of N-methylmorpholine followed by 0.14 g (0.78 mmol) of 2-chloro-4,6-dimethoxy-1,3,5-triazine. The reaction mixture was stirred for 40 minutes and 0.27 g (0.78 mmol) of dimethyl N-(4-amino-4-tert.-butoxycarbonylbutanoyl)-D-aspartate in 1.0 mL of anhydrous dimethylformamide was added. After 2.5 hours, the reaction mixture was diluted with 50% CH$_3$OH/CHCl$_3$ and was concentrated in vacuo and the residue was chromatographed on silica gel with a gradient of 5–7% CH$_3$OH/CHCl$_3$ to yield 0.26 g (54%) of N-(N-{4-[2-(2-amino-4-hydroxy-5,6,7,8-tetrahydropyrido[2,3-d]pyrimidin-6-yl)ethyl]-benzoyl}-L-$\gamma$-glutamyl)-D-aspartic acid 1-tert.-butyl-2,2-dimethyl ester as a white solid. Rf=0.43 (20% CH$_3$OH/CHCl$_3$) m.p. 129°–133° C. (foam, dec); Mass Spectrum (FD+): M+1=643; IR (KBr, cm$^{-1}$)= 645, 732, 773, 847, 1153, 1220, 1305, 1368, 1393, 1439, 1468, 1481, 1502, 1541, 1645, 1740, 2931, 3350; UV (C$_2$H$_5$OH): )$\lambda_{max}$=224, 279 ($\epsilon$=28373, 12315); $^1$H NMR (300 MHz, DMSO$_{d6}$) $\delta$1.38 (s, 9H), 1.53–1.70 (m, 3 H), 1.77–2.02 (m, 3H), 2.21–2.32 (m, 2H), 2.60–2.80 (m, 5H), 3.15–3.18 (m, 1H), 3.58 (s, 3H), 4.23–4.26 (m, 1H), 4.58–4.63 (m, 1H), 5.92 (s, 2H), 6.26 (s, 1H), 7.27 (d, J=8.1 Hz, 2Hz), 7.77 (d, J=8.1 Hz, 2H), 8.39 (d, J=7.8 Hz, 1H), 8.52 (d, J=7.3 Hz, 1H); 9.69 (s, 1H).

D. A solution of 0.116 g (0.18 mmol) of N-(N-{4-[2-(2-amino-4-hydroxy-5,6,7,8-tetrahydropyrido[2,3-d]pyrimidin-6-yl)ethyl]-benzoyl}-L-$\gamma$-glutamyl)-D-aspartic acid 1-tert.-butyl-2,2-dimethyl ester in 10 mL of trifluoroacetic acid was stirred overnight and then concentrated in vacuo. The residue was dried under high vacuum and dissolved in 3.0 mL of 0.5N sodium hydroxide and this mixture was stirred for four hours and then acidified to pH 3 with 1.0N hydrochloric acid to yield 0.070 g (69%) of N-(N-{4-[2-(2-amino-4-hydroxy-5,6,7,8-tetrahydropyrido [2,3-d]pyrimidin-6-yl)ethyl]benzoyl} -L-$\gamma$-glutamyl)-D-aspartic acid as a white solid. m.p. 229°–242° C. (dec); Mass Spectrum (FAB+): M+=559; IR (KBr, cm$^{-1}$)=545, 644, 753, 845, 1018, 1203, 1349, 1397, 1503, 1540, 1651, 1711, 2930, 3336; UV (C$_2$H$_5$OH) $\lambda_{max}$=203, 224, 279 ($\epsilon$=34992, 27290, 12284); $^1$H NMR (300 MHz, DMSO$_{d6}$) $\delta$1.52–1.60 (m, 3H), 1.81–1.93 (m, 2H), 2.01–2.05 (m, 1H), 2.21–2.31 (m,'-2H), 2.51–2.79 (m, 6H), 2.94–3.05 (m, 1H), 4.27–4.34 (m, 1H), 4.45–4.52 (m, 1H), 6.00 (s, 2H), 6.29 (s, 1H), 7.29 (d, J=7.9 Hz, 2H), 7.78 (d, J=7.8 Hz, 2H), 8.22 (d, J=7.8 Hz, 1H), 8.56 (d, J=7.2 Hz, 1H).

EXAMPLE 2

N-(N-{5-[2-(2-Amino-4-hydroxy-5,6,7,8-tetrahydropyrido[2,3-d]primidin-6-yl)ethyl]thien-2-ylcarbony}-L-$\gamma$-glutamyl-D-aspartic Acid A. To a solution of 0.25 g (0.79 mmol) of 5-[2-(amino-4-hydroxy-5,6,7,8-tetrahydropyrido[2,3-d]pyrimidin-6-yl) ethyl]thien-2-ylcarboxylic acid in 4.0 mL of anhydrous dimethylformamide was added 0.20 mL (1.80 mmol) of 4-methylmorpholine and 0.14 g (0.80 mmol) of 2-chloro-4, 6-dimethoxy-1,3,5-triazine. The reaction mixture was stirred at room temperature for 70 minutes, and 0.28 g (0.81 mmol) of dimethyl N-(4-amino-4-tert.-butoxycarbonylbutanoyl)-D-aspartate in 1.0 mL of anhydrous dimethylformamide was added. The reaction mixture was stirred for another 3 hours and then concentrated in vacuo. The crude material was then chromatographed on silica gel using a gradient of 4–10% CH$_3$OH/CHCl$_3$ to give 0.19 g (37%) of N-(N-{5-[2-(2-amino-4-hydroxy-5,6,7,8-tetrahydropyrido[2,3-d] pyrimidin-6-yl)ethyl]thien-2-ylcarbonyl}-L-$\gamma$-glutamyl)-D-aspartic acid 1-tert.-butyl-2,2-dimethyl ester as an off-white solid.; Rf=0.39 (20% CH$_3$OH/CHCl$_3$); Mass Spectrum (FAB+): M+=649; IR (KBr, cm$^{-1}$)=640, 737, 772, 1153, 1220, 1368, 1461, 1545, 1635, 1740, 2929, 3383; UV (ETOH) $\lambda_{max}$=222, 279 ($\epsilon$=25233, 24541); $^1$H NMR (300 MHz, DMSO$_{d6}$) $\delta$1.38 (s, 9H), 1.48–1.60 (m, 3H), 1.77–2.02 (m, 3H), 2.18–2.23 (m, 2H), 2.62–2.86 (m, 6H), 3.14–3.17 (M, 1H), 3.58 (s, 6H), 4.19–4.21 (m, 1H), 4.8–4.60 (m, 1H), 5.72 (s, 2H), 6.26 (s, 1H), 6.89 (s, 1H), 8.40 (d, J=6.2 Hz, 1H), 8.51 (d, J=6.0 Hz), 9.69 (s, 1H).

B. A sample of 0.098 g (0.15 mmol) of N-(N-{5-[2-(2-amino-4-hydroxy-5,6,7,8-tetrahydropyrido[2,3-d] pyrimidin-6-yl)ethyl]thien-2-ylcarbonyl }-L-$\gamma$-glutamyl)-D-aspartic acid 1-tert.-butyl-2,2-dimethyl ester was dissolved in 10 mL of trifluoroacetic acid and stirred overnight. This solution was then concentrated in vacuo and pumped to dryness under high vacuum. This solid material was then dissolved in 3.0 mL of 0.5N sodium hydroxide and stirred for four hours. The reaction mixture was then acidified to pH 3 with 1.0N hydrochioric acid to yield 0.055 g (65%) of N-(N-{5-[2-(2-amino-4-hydroxy-5,6,7,8-tetrahydropyrido

[2,3-d]pyrimidin-6-yl)-ethyl]thien-2-ylcarbonyl}-L-γ-glutamyl)-D-aspartic acid as a white solid. m.p. 246°–262° C. (dec.); Mass Spectrum (FAB+): M+=565.2; IR (KBr, cm$^{-1}$) =545, 643, 724, 754, 801, 1140, 1205, 1266, 1400, 1461, 1548, 1654, 2930, 3356; UV (C$_2$H$_5$OH) λ$_{max}$=222, 279 (ε=17930, 17930); $^1$H NMR (300 MHz, DMSO$_{d6}$) δ1.55–1.68 (m, 3H), 1.81–2.19 (m, 3H), 2.20–2.25 (m, 2H), 2.60–2.89 (m, 6H), 3.07–3.10 (m, 1H), 4.25–4.27 (m, 1H), 4.46–4.90 (m, 1H), 5.88–5.90 (m, 2H), 6.23–6.25 (m, 1H), 6.87 (d, J=3.3 Hz, 1H), 7.65 (d, J=3.5 Hz, 1H), 8.20 (d, J=8.3 Hz, 1H), 8.52 (d, J=8.0 Hz, 1H), 9.82 (br s, 1H).

EXAMPLE 3

N-(N-{4-[2-(2-Amino-4-hydroxy-5,6,7,8-tetrahydropyrido[2,3-d]pyrimidin-6-yl)ethyl]benzoyl}-L-γ-glutamyl)-D-glutamic Acid A. A mixture of 1.12 g (3.31 mmnol) of N-carbobenzyloxy-L-glutamic acid α-tert.-butyl ester in 20 mL of methylene chloride was cooled to 0° C. in an ice bath, and 0.50 mL (3.58 mmol) of triethylamine was added. The reaction mixture was stirred for 15 minutes and 0.49 mL (3.77 mmol) of isobutyl chloroformate was added. The reaction mixture was stirred for 35 minutes at 0° C. and 1.25 g (3.33 mmol) of D-glutamate diethyl ester tosylate and 1.05 mL (7.52 mmol) of triethylamine was added. The reaction mixture was then stirred at 0° C. for 1.5 hours and allowed to warm slowly over 72 hours to room temperature. The reaction mixture was then diluted with 50 mL methylene chloride and was washed sequentially with 5% sodium bicarbonate, 0.5N hydrochloric acid and brine. The organic layer was dried over sodium sulfate, filtered and concentrated in vacuo. The residue was then chromatographed on silica gel eluting with 70% hexanes/EtOAc to give 1.14 g (75%) of diethyl N-[4-(benzyloxycarbonylamino)-4-tert.-butoxycarbonylbutanoyl]-D-glutamate as a thick clear oil. Rf=0.64 (10%CH$_3$OH/CHCl$_3$); Mass Spectrum (FD+): M+1=523; IR (CHCl$_3$, cm$^{-1}$l) =843, 1029, 1053, 1156, 1303, 1348, 1371, 1395, 1455, 1478, 1510, 1675, 1729, 2939, 2984, 3011, 3028, 3425; UW (C$_2$H$_5$OH): λmax=203 (ε=10960); Anal. Calcd. for C$_{26}$H$_{38}$N$_2$O$_9$: C, 59.76; H, 7.33; N, 5.36; Found: C, 59.99; H, 7.15; N, 5.51. $^1$H NMR (300 MHz,CDCl$_3$) δ1.13–1.23 (m, 6H), 1.40 (s, 9H), 1.85–1.95 (m, 2H), 2.06–2.17 (m, 2H), 2.23–2.36 (m, 4H), 4.03–4.23 (m, 5H), 4.45–4.5 (m, 1H), 5.04 (s, 2H), 5.91 (d, J=8.0 Hz, 1H), 7.12 (d, J=7.6 Hz, 1H), 7.24–7.29 (m, 5H).

B. To a solution of 3.12 g (5.9 mmol) of diethyl N-[4-(benzyloxycarbonylamino)-4-tert.-butoxycarbonylbutanoyl]-D-glutamate in 27 mL of anhydrous ethanol was added 0.66 g of 10% Pd/C. The reaction mixture was then stirred under an atmosphere of hydrogen overnight. The catalyst was removed by filtration through Celite® and the filtrate was concentrated in vacuo to give 1.83 g (81%) of diethyl N-(4-amino-4-tert.-butoxycarbonylbutanoyl)-D-glutamate as a white gum. Mass Spectrum (FD+): M+1=389; IR (CHCl$_3$, cm$^{-1}$)=845, 1023, 1156, 1370, 1394, 1448, 1477, 1507, 1602, 1673, 1729, 2983, 3024, 3426, 3690; Anal. Calcd. for C$_{18}$H$_{32}$N$_2$O$_7$: C, 55.66; H, 8.30; N, 7.21.; Found: C, 55.93; H, 8.01; N, 7.26; $^1$H NMR (300 MHz, CDCl$_3$) δ1.22–1.30 (m, 6H), 1.45 (s, 9H), 1.75–1.84 (m, 2H), 1.96–2.02 (m, 2H), 2.14–2.22 (m, 2H), 2.32–2.43 (m, 4H), 4.09–4.22 (m, 5H), 4.58–4.60 (m, 1H), 6.96 (d, J=7.4 Hz, 1H).

C. To 0.21 g (0.60 mmol) of 4-[2-(2-amino-4-hydroxy-5,6,7,8-tetrahydropyrido[2,3-d]pyrimidin-6-yl)ethyl]benzoic acid in a three-necked round bottomed flask under an atmosphere of nitrogen were added 3.5 mL of anhydrous dimethylformamide and 0.14 mL (1.3 mmol) of 4-methylmorpholine. To this reaction mixture was then added 0.11 g (0.61 mmol) of 2-chloro-4,6-dimethoxy-1,3,5-triazine. The reaction was stirred at room temperature for 80 minutes and then 0.40 g (1.03 mmol) of diethyl N-(4-amino-4-tert.-butoxycarbonylbutanoyl)-D-glutamate was added in 1.0 mL of anhydrous dimethylformamide. After 3 hours, the reaction was concentrated in vacuo and the crude product was chromatographed on silica gel eluting with a gradient of 5–7 % CH$_3$OH/CHCl$_3$ to yield 0.22 g (52%) of N-(N-{4-[2-(2-amino-4-hydroxy-5,6,7,8-tetrahydropyrido[2,3-d]pyrimidin-6-yl)ethyl]benzoyl}-L-γ-glutamyl)-D-glutamic acid 1-tert.-butyl-2,2-diethyl ester as a white solid. Rf=0.15 (10% CH$_3$OH/CHCl$_3$); m.p. 143°–146° C. (foam, dec.); Mass Spectrum (FAB+): M+1=685; IR (KBr, cm$^{-1}$l) =574, 773, 847, 1020, 1154, 1304, 1368, 1465, 1480, 1502, 1540, 1645, 1737, 2932, 2980, 3381; UV (C$_2$H$_5$OH) λ$_{max}$= 224, 280 (ε=27153, 12096); $^1$H NMR (300 MHz, DMSO$_{d6}$) δ1.14 (t, J=7.0 Hz, 6H), 1.38 (s, 9H), 1.49–1.55 (m, 3H), 1.75–1.84 (m, 2H), 1.87–1.93 (m, 2H), 1.94–1.98 (m, 1H), 2.21–2.34 (m, 4H), 2.68–2.75 (m, 3H), 3.15 (d, J=10.3 Hz, 1H), 3.97–4-07 (m, 4H), 5.89 (s, 2H), 6.23 (d, J=1.2 Hz, 1H), 7.29 (d, J=7.9 Hz), 7.77 (d, J=7.8 Hz, 2H), 8.25 (d, J=7.5 Hz, 1H), 8.52 (d, J=7.3 Hz, 1H), 9.65 (S, 1H).

D. A solution of 0.12 g (0.18 mmol) of N-(N-{4-[2-(2-amino-4-hydroxy-5,6,7,8-tetrahydropyrido[2,3-d]pyrimidin-6-yl)ethyl]benzoyl}-L-γ-glutamyl)-D-glutamic acid 1-tert.-butyl-2,2-diethyl ester in 10 mL trifluoroacetic acid was stirred at room temperature overnight. The solution was concentrated in vacuo and the solid residue was then dissolved in 3.0 mL of 0.N NAOH and stirred at room temperature for 72 hours. The solution was acidified with 1.0N hydrochloric acid to pH=2–3, and the precipitate was filtered and dried in a vacuum oven at 60° C. to give 0.092 g (71%) of N-(N-{4-[2-(2-amino-4-hydroxy-5,6,7,8-tetrahydropyrido[2,3-d]pyrimidin-6-yl)ethyl]benzoyl}-L-γ-glutamyl)-D-glutamic acid as a tan solid; Mass Spectrum (FAB+): M+=573; IR (KBr, cm$^{-1}$)=550.75, 651, 749, 840, 1189, 1349, 1539, 1635, 1717, 2926, 3381; UV (C$_2$H$_5$OH) λ$_{max}$=224 (ε=28760); $^1$H NMR (300 MHz, DMSO$_{d6}$) δ1.49–1.63 (m, 3H), 1.68–1.95 (m, 4H), 2.00–2.17 (m, 1H), 2.21–2.31 (m, 4H), 2.64–2.81 (m, 3H), 3.17–3.28 (m, 1H), 4.13–4.20 (m, 1H), 4.30–4.33 (m, 1H), 6.20–6.26 (m, 2H), 6.43 (d, J=1.6 Hz, 1H), 7.29 (d, J=7.9 Hz, 2H), 7.79 (d, J=7.9 Hz, 2H), 8.13 (d, J=7.5 Hz, 1H), 8.50 (d, J=7.1 Hz, 1H).

EXAMPLE 4

N-(N-{5-[2-(2-Amino-4-hydroxy-5,6,7,8-tetrahydropyrido[2,3-d]pyrimidin-6-yl)ethyl]thien-2-ylcarbonyl}-L-γ-glutamyl)-D-glutamic Acid A. To 0.15 g (0.43 mmol) of 5-[2-(2-amino-4-hydroxy-5,6,7,8-tetrahydropyrido[2,3-d]pyrimidin-6-yl)ethyl]thien-2-ylcarboxylic acid in a three-necked round bottomed flask under an atmosphere of nitrogen were added 3.0 mL of anhydrous dimethylformamide and 0.12 mL (1.08 mmol) of 4-methylmorpholine followed by 0.085 g (0.48 mmol) of 2-chloro-4,6-dimethoxy-1,3,5-triazine. The reaction mixture was stirred at room temperature for 2.5 hours and 0.20 g (0.51 mmol) of diethyl N-(4-amino-4-tert.-butoxycarbonylbutanoyl)-D-glutamate was then added in 2.0 mL anhydrous dimethylformamide. The reaction mixture was stirred at room temperature for an 4 hours and concentrated in vacuo. The residue was chromatographed on silica gel eluting with 10% CH$_3$OH/CHCl$_3$ to yield 0.050 g (15%) of N-(N-{5-[2-(2-amino-4-hydroxy-5,6,7,8-tetrahydropyrido[2,3-d]pyrimidin-6-yl)ethyl]thien-2- ylcarbonyl) -L-γ-glutamyl}-D-glutamic acid 1-tert.-butyl-2,
2-diethyl ester as a white solid. Rf=0.14 (10% CH$_3$OH/
CHCl$_3$) m.p.=160°–166° C. (foam, dec.); Mass Spectrum
(FAB+): M+=691; IR (KBr, cm$^{-1}$)=641, 773, 810, 1024,
1153, 1219, 1304, 1369, 1462, 1545, 1632, 1737, 2932,
2980, 3371; UV (C$_2$H$_5$OH) λ$_{max}$=222, 279 (ε=25604,
24847); Anal. Calcd. for C$_{32}$H$_{46}$N$_6$O$_9$S: C, 55.64; H, 6.71;
N, 12.17; Found: C, 55.41; H, 6.69; N, 11.98; $^1$H NMR (300
MHz, CDCl$_3$) δ 1.22–1.31 (m, 6H), 1.48 (s, 9H), 1.99–2.45
(m, 12H), 2.64–2.68 (m, 1H), 2.90–2.98 (m, 3H), 3.30–3.34
(m, 1H), 4.08–4.23 (m, 4H), 4.54–4.57 (m, 1H), 4.65–4.66
(m, 1H), 5.10–5.11 (m, 1H), 5.40–5.43 (m, 2H), 6.77 (d,
J=3.0 Hz, 1H), 7.17–7.23 (m, 2H), 7.42 (s, 1H).

B. A solution of 0.036 g (0.052 mmol) of N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-glutamic acid 1-tert.-butyl-2,2-diethyl ester in 1.5 mL of trifluoroacetic acid was stirred at room temperature overnight. The solution was concentrated in vacuo and the solid redissolved in 2.0 mL of 0.5N sodium hydroxide and this solution was stirred overnight and then acidified with 1.0N hydrochloric acid to pH 2–3. The precipitate was filtered, washed with water, and dried in vacuo to give 0.019 g (62%) of N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-glutamic acid as an off-white solid. Exact Mass: Calcd. for 579.1873; Found 579.1829; IR (KBr, cm$^{-1}$) 1250, 1351, 1459, 1546, 1646, 1710, 2927, 3347; UV (C$_2$H$_5$OH) λ$_{max}$=222 (ε=18588); $^1$HNMR (300 MHz, DMSO$_{d6}$) δ1.54–2.17 (m, 8H), 2.18–2.29 (m, 4H), 2.73–2.86 (m, 3H), 3.14–3.22 (M,--1H), 4.15–4.19 (m, 1H), 4.25–4.30 (m, 1H), 5.95 (s, 2H), 6.27 (S, 1H), 6.88 (d, J=3.3 Hz, 1H), 7.67 (d, J=3.4 Hz, 1H), 8.15 (d, J=7.5 Hz, 1H), 8.54 (d, J=7.6 Hz, 1H).

EXAMPLE 5

N-{5-[2-(2-Amino-4-hydroxy-5,6,7,8-tetrahydropyrido[2,3-d]pyrimidin-6-yl)ethyl]thien-2-ylcarbonyl}glycine Ethyl Ester To 0.15 g (0.47 mmol) of 5-[2-(2-amino-4-hydroxy-5,6,7,8-tetrahydropyrido[2,3-d]-pyrimidin-6-yl)ethyl]thien-2-ylcarboxylic acid in a three-necked round bottomed flask under an atmosphere of nitrogen were added 3.0 mL of anhydrous dimethylformamide and 0.11 mL (0.99 mmol) of 4-methylmorpholine. To this was then added 0.84 g (0.48 mmol) of 2-chloro-4,6-dimethoxy-1,3,5-triazine. The reaction mixture was stirred at room temperature for 35 minutes and a solution of 0.072 g (0.51 mmol) of glycine ethyl ester hydrochloride in 1.0 mL of anhydrous dimethylformamide was added together with 0.65 mL (5.85 mmol) of 4-methylmorpholine. After 35 minutes, an additional 0.015 g (0.11 mmol) of glycine ethyl ester hydrochloride and 0.2 mL (1.80 mmol) of 4-methylmorpholine was added. The reaction was stirred for 3 hours and concentrated in vacua. The crude mixture then was chromatographed on silica gel eluting with a gradient of 2–12% CH$_3$OH/CHCl$_3$ to give 0.072 g (38%) of N-{5-[2-(2-amino-4-hydroxy-5,6,7,8-tetrahydropyrido[2,3-d]pyrimidin-6-yl)ethyl]thien-2-ylcarbonyl}glycine ethyl ester as a white solid. Rf=0.34 (20% CH$_3$OH/CHCl$_3$) m.p.=152°–160° C. (foam, dec.) Mass Spectrum (FD+): M+=405; IR (CHCl$_3$, cm$^{-1}$)=1046, 1196, 1304, 1464, 1602, 1745, 2363, 2977, 3025, 3619; UV (C$_2$H$_5$OH) λ$_{max}$=222, 279 (ε=24333, 23816); $^1$H NMR (300 MHz, DMSO$_{d6}$) δ1.17 (t, J=6.5 Hz, 3H), 1.52–1.60 (m, 3H), 1.77–1.84 (m, 1H), 2.40–2.44 (m, 1H), 2.72–2.8(m, 3H), 3.14–3-24 (m, 1H), 3.91 (d, J=4.7 Hz, 2H), 4.05–4.12 (m, 2H), 6.24 (s, 2H), 6.89 (s, 1H, 7.57 (s, 1H), 8.80 (s, 1H), 9.66 (s, 1H).

EXAMPLE 6

N-{5-[2-(2-Amino-4-hydroxy-5,6,7,8-tetrahydropyrido[2,3-d]pyrimidin-6-yl)ethyl]thien-2-ylcarbonyl}glycine A solution of 0.052 g (0.13 mmol) of N-{5-[2-(2-amino-4-hydroxy-5,6,7,8-tetrahydropyrido[2,3-d]pyrimidin-6-yl) ethylthien-2-ylcarbonyl}glycine ethyl ester in 2.5 mL of 0.5N sodium hydroxide was stirred overnight at room temperature. The solution was acidified to pH 2–3 with 1.0N hydrochloric acid and the solid collected, washed with water, and dried in a vacuum oven to give 0.037 g of N-{5-[2-(2-amino-4-hydroxy-5,6,7,8-tetrahydropyrido[2,3-d]pyrimidin-6-yl)-ethyl]thien-2-ylcarbonyl}glycine as a white solid. Rf=0.12 (1:1 CH$_3$OH/CHCl$_3$); Mass Spectrum (FAB+): M+=378; IR (KBr, cm$^{-1}$)=504, 549, 580, 657, 748, 815, 1019, 1215, 1238, 1354, 1399, 1489, 1542, 1638, 1719, 2928, 3243, 3378. $^1$H NMR (300 MHz, DMSO$_{d6}$/TFA$_{d4}$) δ1.54–1.69 (m, 3H), 1.84 1.92 (m, 1H), 2.42–2.51 (m, 1H), 2.78–2.89 (m, 3H), 3.31 (d, J=12.1 Hz, 1H), 3.84 (s, 2H), 6.87 (d, J=3.6 Hz, 1H), 7.57 (d, J=3.6 Hz, 1H).

EXAMPLE 7

N-(N-{5-[2-(2-Amino-4-hydroxy-5,6,7,8-tetrahydropyrido[2,3-d]pyrimidin-6-yl)ethyl]thien-2-ylcarbonyl}-γ-L-glutamyl)-D-glutamate tris-(tert.-Butyl) Ester To a reaction mixture of 0.16 g (0.46 mmol) of 5-[2-(2-amino-4-hydroxy-5,6,7,8-tetrahydropyrido[2,3-d]pyrimidin-6-yl)ethyl]thien-2-ylcarboxylic acid in 4.0 mL of anhydrous dimethylformamide and 0.06 mL (0.55 mmol) of 4-methylmorpholine was added under a nitrogen atmosphere 0.091 g (0.52 mmol) 2-chloro-4,6-dimethoxyl,3,5-triazine. The reaction was stirred at room temperature for 40 minutes and 0.24 g (0.54 mmol) of N-(γ-L-glutamyl)-D-glutamate-tris-(tert.-butyl) ester in 2.0 mL of anhydrous dimethylformamide was added. The reaction mixture was stirred at room temperature overnight and then concentrated in vacuo. The crude residue was then chromatographed on silica gel eluting with a gradient of 2–10% CH$_3$OH/CHCl$_3$ to give 0.088 g (23%) of N-(N-{5-[2-(2-amino-4-hydroxy-5,6,7,8-tetrahydropyrido[2,3 -d]pyrimidin-6-yl)ethyl]thien-2-ylcarbonyl}-γ-L-glutamyl)-D-glutamate tris-(tert.-butyl) ester as a white solid; Rf=0.13 (10% CH$_3$OH/CHCl$_3$); m.p. 151°–160° C. (foam, dec.); Mass Spectrum (FD+): M+1= 748; IR (KBr, cm$^{-1}$)=843, 1047, 1154, 1305, 1369, 1394, 1463, 1482, 1509, 1544, 1602, 1642, 1726, 2933, 2982, 3007, 3332, 3414; UV (C$_2$H$_5$OH) λ$_{max}$=222, 279 (ε=26778, 25396); $^1$HNMR (300 MHz, CDCl$_3$) δ1.43 (s, 9H), 1.44 (s, 9H), 1.47 (s, 9H), 1.60–1.74 (m, 2H), 1.89–2.19 (m, 7H), 2.20–2.44; (m, 5H), 2.64–2.68 (m, 1H), 2.89–2.97 (m, 3H), 3.28–3.33 (m, 1H), 4.43–4.50 (m, 1H), 4.53–4.58 (m, 1H), 5.34–5.35 (m, 2H), 5.65–5.67 (m, 2H), 6.74 (d, j=2.3 Hz, 1H), 6.93 (q, J=7.8 Hz, 1H), 7.39–7.42 (m, 2H).

EXAMPLE 8

N-{5-[2-(2-Amino-4-hydroxy-5,6,7,8-tetrahydropyrido[2,3-d]pyrimidin-6-yl)-ethyl]thien-2-ylcarbonyl]}-L-homocysteic Acid α-Methyl Ester A. To a solution of 0.99 g (5.4 mmol) of L-homocysteic acid in 45 mL of anhydrous methanol at 0° C. were added 9.0 mL of thionyl chloride. The mixture was stirred overnight [*J. Med. Chem.*, 27, 603 (1984)]. The resulting clear solution was then concentrated in vacuo to give 1 g (93%)

of L-homocysteic acid α-methyl ester hydrochloride as a fine white solid. Mass Spectrum (FAB+): M+=233; IR (KBr, cm$^{-1}$) =538, 608, 751, 780, 984, 1031, 1045, 1083, 1213, 1243, 1335, 1441, 1454, 1522, 1632, 1743, 2958, 3430; $^1$H NMR (300 MHz, D20) δ2.28–2.41 (m, 2H), 3.02–3.09 (m, 2H), 3.82 (s, 3H), 4.30 (t, J=6.5 Hz, 1H).

B. To a solution of 0.106 g (0.33 mmol) of 5-[2-(2-amino-4-hydroxy-5,6,7,8-tetrahydropyrido[2,3-d]pyrimidin-6-yl)ethyl]thien-2-ylcarboxylic acid in 2.0 mL anhydrous dimethylformamide and 0.045 mL (0.41 mmol) of 4-methylmorpholine was added 0.058 g (0.33 mmol) of 2-chloro-4,6-dimethoxy-1,3,5-triazine. The reaction mixture was stirred for 30 minutes at room temperature and 0.084 g (0.36 mmol) of α-methyl ester L-homocysteic acid hydrochloride was added in 1.0 mL anhydrous dimethylformamide and 0.08 mL (0.72 mmol) of 4-methylmorpholine. The reaction mixture was stirred at room temperature for an additional 3 hours and then concentrated in vacuo. The residue was then purified on a Chromatotron® silica gel plate, eluting with a gradient of 100% EtOAc to 10% CH$_3$OH/CHCl$_3$ to 75/25/1 (CHCl$_3$/CH$_3$OH/NH$_4$OH) to give 0.044 g (27%) of N-{5-[2-(2-amino-4-hydroxy-5,6,7,8-tetrahydropyrido[2,3-d]pyrimidin-6-yl)-ethyl]thien-2-ylcarbonyl}-L-homocysteic acid α-methyl ester as an off-white solid. Rf=0.68 (50/50/2:CHCl$_3$/CH$_3$OH/NH$_4$OH); m.p. 221°–226° C. (foam, dec.); Mass Spectrum (FD+): M+1=501; IR (CHCl$_3$, cm$^{-1}$)=500, 528, 656, 748, 800, 1017, 1038, 1134, 1207, 1279, 1353, 1405, 1457, 1545, 1642, 1696, 3129; UV ((C$_2$H$_5$OH) λ$_{max}$=222, 279 (ε=21585, 21991); $^1$H NMR (300 MHz, DMSO$_{d6}$) δ1.58–1.69 (m, 3H), 1.89–1.95 (m, 2H), 2.04–2.12 (m, 3H), 2.87–2.90 (m, 3H), 3.14 (s, 1H), 3.23–3.34 (m, 1H), 3.61 (s, 3H), 4.36–4.38 (m, 1H), 6.89 (d, J=1.7 Hz, 1H), 6.97 (s, 1H), 7.14 (s, 1H), 7.31 (s, 1H), 7.65 (d, J=2.7 Hz, 2H), 9.09 (d, J=6.2 Hz, 1H).

EXAMPLE 9

N-{5-[2-(2-Amino-4-hydroxy-5,6,7,8-tetrahydropyrido[2,3-d]pyrimidin-6-yl)-ethyl]thien-2-ylcarbonyl}-L-homocysteic Acid A solution of 0.022 g (0.066 mmol) of N-{5-[2-(2-amino-4-hydroxy-5,6,7,8-tetrahydropyrido[2,3-d]pyrimidin-6-yl)-ethyl]thien-2-ylcarbonyl}-L-homocysteic acid α-methyl ester in 0.6 mL of 0.5N sodium hydroxide was stirred at room temperature overnight. The solution was then acidified with 1.0N hydrochloric acid to pH 2–3, and the precipitate was filtered, washed with water, and dried in vacuo to give 0.018 g (84%) of N-{5-[2-(2-amino- 4-hydroxy-5,6,7,8-tetrahydropyrido[2,3-d]pyrimidin-6-yl)-ethyl]thien-2-ylcarbonyl}-L-homocysteic acid as a tan solid; Exact Mass= Calcd. for 486.1117; Found 486.1103; IR (KBr, cm$^{-1}$)=544, 751, 1038, 1206, 1351, 1460, 1547, 1653, 1700, 2926, 3363; UV (0.1N NaOH) λ$_{max}$=218 (ε=18619); $^1$H NMR (300 MHz, DMSO$_{d6}$/TA$_{d4}$) δ1.57–1.70 (m, 3H), 1.842.17 (m, 4H), 2.63–2.68 (m, 2H), 2.82–2.89 (m, 3H), 3.30 (d, J=13.3 Hz, 1H), 4.35 (dd, 1H, J=7.4, 4.84 Hz), 6.86 (d, J=3.3 Hz, 1H), 7.66 (d, J=3.5 Hz, 1H).

EXAMPLE 10

N-{5-[2-(2-Amino-4-hydroxy-5,6,7,8-tetrahydropyrido[2,3-d]pyrimidin-6-yl)-ethyl]thien-2-ylcarbonyl}hydroxylamine To 10 mL of anhydrous methanol was added 0.33 g (14.4 mmol) of sodium metal and a solution of 0.050 g (0.72 mmol) of hydroxylamine hydrochloride in 7 mL of methanol was then added. The resulting reaction mixture was stirred for 15 minutes and 0.23 g (0.5 mmol) of methyl 5-[2-(2-pivaloylamino-4-hydroxy-5,6,7,8-tetrahydropyrido[2,3-d]pyrimidin-6-yl)ethyl]thien-2-ylcarboxylate was added under nitrogen. The reaction mixture was stirred for 30 minutes, 0.011 g (0.16 mmol) of hydroxylamine hydrochloride was added, and the reaction was stirred a total of 4.5 hours, and then filtered. The filtrate was then treated with diethyl ether and the solid collected and dried in vacuo to give 0.13 g (71%) of N-{5-[2-(2-amino-4-hydroxy-5,6,7,8-tetrahydropyrido[2,3-d]pyrimidin-6-yl)ethyl]thien-2-ylcarbonyl}hydroxylamine as a tan colored solid. Rf=0.09 (10% CH$_3$OH/CHCl$_3$); $^1$H NMR (300 MHz, DMSO$_{d6}$/TFA$_{d4}$) δ1.55–1.70 (m, 4H), 1.83; 1.91 (m, 1H), 2.82–2.87 (m, 4H), 3.29–3.33 (m, 1H), 6.82 (d, J=3.6 Hz, 1H), 7.43 (d, J=1.4 Hz, 1H);

EXAMPLE 11

1,3-bis-(Tetrazol-5-yl)-1-{4-[2-(2-amino-4-hydroxy-5,6,7,8-tetrahydropyrido[2,3d]pyrimidin-6-yl)ethyl]benzoylamino}propane Diammonium Salt After flame drying a 15 mL two-neck round bottom flask under argon, 0.15 g (0.43 mmol) of 4-[2-(2-amino-4-hydroxy-5,6,7,8-tetrahydropyrido[2,3-d]pyrimidin-6-yl)ethyl]benzoic acid hydrochloride was suspended in 2 mL of anhydrous N,N-dimethylformamide, followed by the addition of 0.14 mL (1.28 mmol) of 4-methylmorpholine. After stirring the reaction mixture at room temperature for 15 minutes, 0.111 g (0.64 mmol) of 2-chloro-4,6-dimethoxy-1,3,5-triazine was added. The reaction was stirred at room temperature for 30 minutes, 0.125 g (0.624 mmol) of 1-amino-1,3-bis-(tetrazol-5-yl)propane was added, and the reaction mixture was stirred at room temperature for an additional 3 hours. The volatiles were removed in vacuo, and the residue was treated with 10 mL of water and the white solid collected by filtration, and dried in a vacuum oven at 60° C. The solid was loaded onto a 4 mm Chromatotron® silica gel plate and eluted with a gradient of 10% CH$_3$OH/CHCl$_3$ to 70:25:5 CHCl$_3$/CH$_3$OH/NH$_4$OH. The correct fractions were combined and concentrated in vacuo to give 0.090 g (40%) of 1,3-bis-(tetrazol-5-yl)-1-{4-[2-(2-amino-4-hydroxy-5,6,7,8-tetrahydropyrido[2,3d]pyrimidin-6-yl)ethyl]benzoylamino}propane diammonium salt as a white solid. Rf=0.11 (6:3.2:0.8) (CHCl$_3$/CH$_3$OHNH$_4$OH); m.p. 226°–229° C. (foam); IR (KBr, cm$^{-1}$)=512, 774, 1109, 1345, 1459, 1538, 1634, 3401; UV (C$_2$H$_5$OH) λ$_{max}$=279, 224, 204 (ε=12391, 28588, 35911) Exact Mass: Calcd=492.2332; Found=492.2306; $^1$H NMR (300 MHz, DMSO$_{d6}$) δ1.50–1.60 (m, 4H), 1.77–1.85 (m, 1H), 2.14–2.28 (m, 2H), 2.47–2.70 (m, 6H), 5.29–5.39 (m, 1H), 5.97 (s, 2H), 6.25 (S, 1H), 7.26 (d, J=8.1 Hz, 211), 7.81 (d, J=7.7 Hz, 2H), 8.66 (q, J=3.5 Hz, 1H).

EXAMPLE 12

2-{4-[2-(2-Amino-4-hydroxy-5,6,7,8-tetrahydropyrido[2,3-d]pyrimidin-6-yl)ethyl]benzoylamino}-3-(2H-tetrazol-5-yl)propanoic Acid Diammonium Salt After flame drying a 15 mL two-neck round bottom flask under argon, 0.20 g (0.57 mmol) of 4-[2-(2-amino-4-hydroxy-5,6,7,8-tetrahydropyrido[2,3-d]pyrimidin-6-yl)ethyl]benzoic acid hydrochloride was suspended in 2 mL of anhydrous N,N-dimethylformamide, followed by the addition of 0.19 mL (1.7 mmol) of 4-methylmorpholine. The reaction mixture was stirred at room temperature for 15 minutes, and 0.15 g (0.86 mmol) of 2-chloro-4,6-dimethoxy-1,3,5-triazine was added. The reaction mixture was stirred at room temperature for an additional 30 minutes and 0.135 g (0.86 mmol) of L-2-amino-3-(2H-tetrazol-5-yl)propanoic acid then was added. The reaction mixture was stirred at room temperature for 3 hours, the volatiles removed in vacuo, and the residue treated with 50 mL of water. The white solid was filtered and dried in a vacuum oven at 60° C. The crude solid was purified by rotary chromatography on a 2 mm Chromatotron® silica gel plate, and eluted with a gradient of 20% $CH_3OH/CHCl_3$ to 60:30:10 $CHCl_3/CH_3OH/NH_4OH$. The correct fractions were combined and concentrated in vacuo to give 0.12 g (43%) of 2-{4-[2-(2-amino-4-hydroxy-5,6,7,8-tetrahydropyrido[2,3-d]pyrimidin-6-yl)ethyl]benzoylamino}-3-3-(2H-tetrazol-5-yl)propanoic acid diammonium salt. Rf 0.21 (5:3.5:1.5) ($CHCl_3/CH_3OH/NH_4OH$); m.p. 221°–222° C. (foam); IR (KBr, cm$^{-1}$)=817, 857, 951, 1106, 1159, 1308, 1402, 1463, 1548, 1615, 3162; UV (0.1N NaOH) $\lambda_{max}$=273, 242, 216 ($\epsilon$=8931, 13640, 22182); Exact Mass: Calcd=454.1951; Found=454.1950; $^1H$ NMR (300 MHz, DMSO$_{d6}$) $\delta$1.48–1.59 (m, 4H), 1.75–1.83 (m, 1H), 2.62–2.76 (m, 4H), 3.73 (quintet, J=6.1 Hz, 2H), 4.55–4-61 (m, 1H), 5.91 (s, 2H), 6.22 (s, 1H), 7.29 (d, J=8.0 Hz, 2H), 7.71 (d, J=7.9 Hz, 2H), 8.72 (d, J=7.3 Hz, 1H), 9.70 (br s, 1H).

EXAMPLE 13

2-{5-[2-(2-Amino-4-hydroxy-5,6,7,8-tetrahydropyrido[2,3-d]pyrimidin-6-yl ethyl]thien-2-ylcarbonylamino}-3-(2H-tetrazol-5-yl)propanoic Acid Diammonium Salt After flame drying a 15 mL two-neck round bottom flask under argon, 0.18 g (0.57 mmol) of 5-[2-(2-amino-4-hydroxy-5,6,7,8-tetrahydropyrido[2,3-d]pyrimidin-6-yl)ethyl]-thien-2-ylcarboxylic acid was suspended in 2 mL of anhydrous N,N-dimethylformamide, followed by the addition of 0.19 mL (1.7 mmol) of 4-methylmorpholine. After allowing the reaction mixture to stir at room temperature for 15 minutes, 0.15 g (0.86 mmol) of 2-chloro-4,6-dimethoxyl,3,5-triazine was added. The reaction was stirred at room temperature for 30 minutes, 0.135 g (0.86 mmol) of amino-3-(2H-tetrazol-5-yl)propanoic acid was added, and the reaction mixture was stirred at room temperature for an additional 3 hours. The volatiles were removed in vacuo, and the residue was treated with 50 mL of water and the solid was filtered and dried in a vacuum oven at 60° C. The crude solid was purified using rotary chromatography on a 2 mm Chromatotron® silica gel plate, and eluted with a gradient of 20% $CH_3OH/CHCl_3$ to 60:30:10 $CHCl_3/CH_3OH/NH_4OH$. The correct fractions were combined and concentrated in vacuo to give 0.050 g (18%) of 2-{5-[2-(2-amino-4-hydroxy-5,6,7,8-tetrahydropyrido[2,3-d]-pyrimidin-6-yl)ethyl]thien-2-ylcarbonylamino}-3-(2H-tetrazol-5-yl) propanoic acid diammonium salt as a white solid. Rf 0.22 (5:3.5:1.5) ($CHCl_3/CH_3OH/NH_4OH$); m.p. 228° C. (foam); IR (KBr, cm$^{-1}$)=553, 616, 746, 814, 1098, 1307, 1396, 1460, 1546, 1617, 3216; UV (0.1N NaOH) $\lambda_{max}$=277, 217 ($\epsilon$=19367, 19896); Exact Mass: Calcd=460.1515; Found= 460.1508; $^1H$ NM (300 MHz, DMSO$_{d6}$) $\delta$1.52–1.64 (m, 3H), 1.76–1.84 (m, 1H), 2.51–2.88 (m, 3H), 3.07–3.23 (m, 4H), 4.45–4.51 (m, 1H), 5.92 (s, 2H), 6.23 (s, 1H), 6.86 (d, J=3.1 Hz, 1H), 7.50 (d, J=3.4 Hz, 1H), 8.56 (d, J=7.3 Hz, 1H);

EXAMPLE 14

2-{4-[2-(2-Amino-4-hydroxy-5,6,7,8-tetrahydropyrido[2,3-d]pyrimidin-6-yl)ethyl]benzoylamino}bicyclo[2.2.1]heptane-2-carboxylic Acid Ammonium Salt After flame drying a 15-mL two-neck round bottom flask under argon, 0.20 g (0.57 mmol) of 4-[2-(2-amino-4-hydroxy-5,6,7,8-tetrahydropyrido[2,3-d]pyrimidin-6-yl)ethyl]-benzoic acid hydrochloride was suspended in 2 mL of anhydrous N,N-dimethylformamide, followed by the addition of 0.19 mL (1.7 mmol) of 4-methylmorpholine. After stirring the reaction at room temperature for 15 minutes, 0.15 g (0.86 mmol) of 2-chloro-4,6-dimethoxy-1,3,5-triazine was added. The reaction was stirred at room temperature for 30 minutes and 0.134 g (0.86 mmol) of 2-aminonorbornane-2-carboxylic acid was added. The reaction mixture was stirred at room temperature for 3 hours. The volatiles were concentrated in vacuo, and the residue was treated with 50 mL of H2O, and the white solid was filtered and dried in a vacuum oven at 60° C. The crude solid was purified using rotor chromatography on a 2 mm Chromatotron® silica gel plate, and eluted with a gradient of 20% $CH_3OH/CHCl_3$ to 75:25:1 $CHCl_3/CH_3OH/NH_4OH$. The correct fractions were combined and removed in vacuo to give 0.025 g (9%) of 2-{4-[2-(2-amino-4-hydroxy-5,6,7,8-tetrahydropyrido[2,3-d]pyrimidin-6-yl)ethyl]benzoylamino}bicyclo[2.2.]heptane-2-carboxylic acid ammonium salt as a white solid. Rf=0.30 (6/3.2/0.8) ($CHCl_3/CH_3OH/NH_4OH$); m.p. 241° C. (foam); IR (KBr, cm$^{-1}$)=615, 647, 772, 1019, 1121, 1218, 1307, 1370, 1477, 1538, 1641, 2952, 3344; UV (0.1N NaOH) $\lambda_{max}$=273, 241, 218 ($\epsilon$=9839, 14408, 21458); Exact mass: Calcd=452.2298; Found=452.2338 5; $^1H$ NMR (300 MHz, DMSO$_{d6}$) $\delta$1.26–1.37 (m, 2H), 1.48–1.81 (m, 7H), 1.84–1.88 (m, 4H), 2.63–2.83 (m, 4H), 3.19–3.27 (m, 2H), 5.97 (s, 2H), 6.27 (S, 1H), 7.31 (d, J=8.1 Hz, 2H), 7.78 (d, J=7.9 Hz, 2H), 8.53 (s, 1H).

EXAMPLE 15

Ammonium 1-{5-[2-(2-amino-4-hydroxy-5,6,7,8-tetrahydropyrido[2,3-d]pyrimidin-6-yl)ethyl]thien-2-ylcarbonylamino}cyclohexane-1-carboxylate To a flame-dried three-neck 25 mL round bottom flask under nitrogen was added 0.2 g (0.62 mmol) of 5-[2-(2-amino-4-hydroxy-5,6,7,8-tetrahydropyrido[2,3-d]pyrimidin-6-yl)ethylthien-2-yl]carboxylic acid in 6 mL of anhydrous N-methylpyrrolidinone, followed by 0.20 mL (1.86 mmol) of 4-methylmorpholine and 0.25 g (0.93 mmol) of 25 phenyl N-phenylphosphoramidochloridate. The mixture was heated at 75° C. for 45 minutes, 0.133 g (0.93 mmol) of 1-amino-1-cyclohexanecarboxylic acid was added, and the reaction mixture was heated at 95° C. for 22 hours. The solvent was concentrated under vacuum (0.5 mm Hg at 70° C.) and the residue was triturated in 100 mL of water, filtered, washed with water, and dried in a vacuum oven at 60° C. The crude solid was loaded onto a 2 mm Chromatotron® silica gel plate, and eluted with a gradient of 20% $CH_3OH/CHCl_3$ to 70/25/5 $CHCl_3/meOH/NH_4OH$. The correct fractions were combined and removed in vacuo to give 0.047 g (16%) of ammonium 1-{5-[2-(2-amino-4-hydroxy-5,6,7,8-tetrahydropyrido[2,3-d]pyrimidin-6-yl)ethyl]thien-2-ylcarbonylamino}cyclohexane-1-carboxylate as a white solid. Rf 0.25 (6/3.2/0.8) ($CHCl_3/CH_3OHONH_4OH$), m.p. 211° C. (foam); IR (KBr, cm$^{-1}$)= 515, 545, 612, 747, 772, 1117, 1164, 1220, 1305, 1346, 1388, 1457, 1543, 1653, 1700, 2854, 2925, 3386; UV (0.1N NaOH) $\lambda_{max}$=277, 216 ($\epsilon$=20571, 22222); Exact Mass: Calcd=446.1862; Found=446.1881; $^1H$ NMR (300 MHz, DMSO$_{d6}$) $\delta$1.42–1.72 (m, 11H), 1.73–1.86 (m, 1H), 2.10–2.14 (m, 2H), 2.77–2.88 (m, 3H), 3.18–3.22 (m, 2H), 6.00 (s, 2H), 6.90 (d, j=3.4 Hz, 1H), 7.71 (d, 30 J=3.5 Hz, 1H), 8.04 (s, 1H).

EXAMPLE 16

Ammonium 1-{5-[2-(2-Amino-4-hydroxy-5,6,7,8-tetrahydropyrido[2,3-d]pyrimidin-6-yl)ethyl]thien-2-ylcarbonylamino }cyclopropane-1-carboxylate To a flame-dried three-neck 25 mL round bottom flask under nitrogen was added 0.2 g (0.62 mmol) of 5-[2-(2- amino-4-hydroxy-5,6,7,8-tetrahydropyrido[2,3-d]pyrimidin-6-yl)ethylthien-2-yl]carboxylic acid in 6 mL of anhydrous N-methylpyrrolidinone, followed by 0.20 mL (1.86 mmol) of 4-methylmorpholine and 0.25 g (0.93 mmol) of phenyl N-phenylphosphoramidochloridate. The mixture was heated at 75° C. for 45 minutes, 0.094 g (0.93 mmol) of 1-amino-1-cyclopropanecarboxylic acid was added, and the reaction mixture then heated to 95° C. for 22 hours. The solvent was removed under vacuum (0.5 mmHg at 70° C.), and the residue triturated in 100 mL of water, filtered, washed with water, and dried in a vacuum oven at 60° C. The solid was loaded onto a 2 mm Chromatotrong silica gel plate, and eluted with a gradient of 20% $CH_3OH/CHCl_3$ to 70/25/5 $CHCl_3/CH_3OH/NH_4OH$. The correct fractions were combined and concentrated in vacuo to give 0.047 g (16%) of ammonium 1-{5-[2-(2-amino-4-hydroxy-5,6,7,8-tetrahydropyrido[2,3-d]pyrimidin-6-yl)ethyl]thien-2-ylcarbonylamino}cyclopropane-1-carboxylate as a white solid. Rf 0.18 (6/3.2/0.8) ($CHCl_3/CH_3OH/NH_4OH$); m.p. 231° C. (foam); IR (KBr, $cm^{-1}$)=593, 747, 772, 812, 938, 1033, 1233, 1306, 1346, 1399, 1460, 1544, 1621, 2923, 3332; UV (0.1N NaOH) ) $\lambda_{max}$=277, 216 ($\epsilon$=21036, 23197); Exact Mass: Calcd=404.1393; Found=404.1429 $^1H$ NMR (300 MHz, $DMSO_{d6}$) $\delta$1.00 (s, 2H), 1.31 (s, 2H), 1.56–1.68 (m, 3H), 1.80–1.88 (m, 1H), 2.76–2.93 (m, 4H), 6.06 (br s, 2H), 6.27 (s, 1H), 6.88 (d, j=3.4 Hz, 1H), 7.58 (d, J=3.4 Hz, 1H), 8.79 (s, 1H).

EXAMPLE 17

1-{5-[2-2-Amino-4-hydroxy-5,6,7,8-tetrahydropyrido[2,3-d]pymidin-6-yl)ethyl]thien-2-ylcarbonylamino}cyclopentane-1-carboxylic Acid To a flame-dried three-neck 50 mL round bottom flask under nitrogen was added 0.2 g (0.62 mnmol) of 5-[2-(2-amino-4-hydroxy-5,6,7,8-tetrahydropyrido[2,3-d]pyrimidin-6-yl)ethylthien-2-yl]carboxylic acid in 6 mL of anhydrous N-methylpyrrolidinone, 0.20 mL (1.86 mmol) of 4-methylmorpholine and 0.25 g (0.93 mmol) of phenyl N-phenylphosphoramidochloridate. The mixture was heated at 75° C. for 45 minutes, 0.12 g (0.93 mmol) of 1-amino-1-cyclopentanecarboxylic acid, was added, and the reaction mixture heated at 95° C. for 22 hours. The mixture was concentrated under vacuum (0.5 mm Hg at 70° C.), and this residue was triturated in 100 mL of water, filtered, washed with water, and dried in a vacuum oven at 60° C. The solid was loaded onto a 2 mm Chromatotron® silica gel plate, and eluted with a gradient of 20% $CH_3OH/CHCl_3$ to 70/25/5 $CHCl_3/CH_3OH/ H_4OH$. The correct fractions were combined and concentrated in vacuo to give a white solid which was further purified by loading the sample onto an anion exchange column and eluted with 3N acetic acid to give 0.015 g (6%) of 1-{5-[2-(2-amino-4-hydroxy-5,6,7,8-tetrahydropyrido[2,3-d]pyrimidin-6-yl)ethyl]thien-2-ylcarbonylamino}cyclopentane-1-carboxylic acid as a white solid. Rf=0.29 (6/3.2/0-8) ($CHCl_3/CH_3OH/NH_4OH$) m.p. 229° C. (foam); IR (KBr, $cm^{-1}$)=545, 613, 759, 1121, 1220, 1264, 1309, 1346, 1392, 1457, 1522, 1544, 1637, 1696, 2930, 3379; UV (0.1N NaOH) $\lambda_{max}$=277, 216 ($\epsilon$=17094, 19845); Exact Mass: Calcd=432.1706; Found=432.1726; $^1H$ NMR (300 MHz, $DMSO_{d6}$) $\delta$1.42–1.60 (m, 6H), 1.63–2-00 (m, 7H), 2.33–2.46 (m, 1H), 2.68–2.88 (m, 3H), 5.89 (s, 2H), 6.23 (S, 1H), 6.84 (d, J=3.0 Hz, 1H), 7,58 (d, J=3.2 Hz, 1H), 8.35 (s, 1H), 9.87 (br s, 1H).

EXAMPLE 18

Methyl 1-{5-[2-(2-Amino-4-hydroxy-5,6,7,8-tetrahydropyrido[2,3-d]pyrimidin-6-yl)ethyl]thien-2-ylcarbonyl}pyrrolidine-3-carboxylate A. A solution of 4.29 g (48.9 mmol) of 3-hydroxypyrrolidine in 30 mL of 2N potassium hydroxide was cooled to 0° C. and 10.2 mL of benzyl chloroformate were added with stirring. The reaction was stirred for four hours at 0° C. and then extracted with ethyl acetate (3×100 mL). The extracts were combined, washed with brine, dried over sodium sulfate, filtered, and concentrated in vacua. The residue was chromatographed on silica gel with 70/30 hexanes/ethyl acetate. The correct fractions were combined and concentrated in vacuo to give 8.87 g (81%) of benzyl 3-hydroxypyrrolidine-1-carboxylate as a viscous clear oil. Rf=0.11 in 50/50 hexanes/ethyl acetate Mass Spectrum (FD+): M+221; IR ($CHCl_3$, $cm^{-1}$): 913, 977, 993, 1100, 1117, 1175, 1236, 1360, 1427, 1454, 1498, 1694, 2884, 2954, 3013, 3020, 3436 (broad), 3610; UV ($C_2H_5OH$) $\lambda_{max}$=205 ($\epsilon$=9112), 264 ($\epsilon$=142); $^1H$ NMR (300 MHz, $CDC_{l3}$) $\delta$: 1.91–2.05 (m-, 2H); 3.00 (broad s, 1H); 3.39–3.61 (m, 4H); 4.41 (s, 1H); 5.12 (s, 2H); 7.30–7.43 (m, 5H).

B. Twelve grams (54.2 mmol) of benzyl 3-hydroxypyrrolidine-1-carboxylate were dissolved in 150 mL of pyridine. This solution was cooled to 0° C. in an ice/water bath and 23.66 g (124.5 mmol) of p-toluenesulfonyl acid chloride were added at once. The reaction was allowed to stand at refrigerator temperatures for 18 hours and then acidified with 5N hydrochloric acid to pH<2. This residue was extracted with ethyl acetate (4×200 mL). The extracts were combined, washed with brine, dried over sodium sulfate, filtered, and concentrated in vacua. The residue was chromatographed on silica gel with 50% ethyl acetate/hexane and the product eluted to give 13.4 g (66%) of benzyl 3-p-methylbenzene-sulfonyloxy)pyrrolidine-1-carboxylate as an orange oil. Rf=0.49 (1/1 hexanes/ethyl acetate); Mass Spectrum (FD+): M+=375; IR ($CHCl_3$, $cm^{-1}$): 815, 837, 899, 953, 1020, 1050, 1086, 1115, 1175, 1307, 1359, 1425, 1452, 1497, 1600, 1699, 2897, 3692; UV ($C_2H_5OH$) $\lambda_{max}$=226 ($\epsilon$=11821), 263 ($\epsilon$=725), 274 ($\epsilon$=439); Anal. Calcd. for $C_{19}H_{21}N_1O_5S$: C,60.78; H,5.64; N,3.73; S, 8.54. Found: C, 60.57; H, 5.69; N, 3.52; S, 8.56; $^1H$ NMR (300 MHz,$CDCl_3$) $\delta$1.96–2.13 (m, 2H); 2.42 (s, 3H); 3.43–3.62 (m, 4H); 5.05 (s, 1H); 5.10 (s, 2H); 7.33 (s, 7H); 7.77 (d, j=7.9 Hz, 2H).

C. To a solution of 13.4 g (35.7 mmol) of benzyl 3-(p-methylbenzenesulfonyloxy)pyrrolidine-1-carboxylate in 49 mL of DMSO were added 2.58 g (50.6 mmol) of finely powdered sodium cyanide. The reaction mixture was heated at 80° C. for 3.5 hours and then cooled to room temperature. The crude was diluted with 100 mL of brine and extracted with diethyl ether (5×250 mL). The extracts were combined, washed with brine, dried over sodium sulfate, filtered and concentrated in vacuo. The residue was chromatographed on silica gel with 60% ethyl acetate/hexanes to give 6.8 g (83%) of benzyl 3-cyanopyrrolidine-1-carboxylate as a clear oil. Rf=0.46 in 100% ethyl acetate; Mass Spectrum (FD+): M+=230; IR ($CHCl_3$, $cm^{-1}$): 882, 912, 986, 1030, 1119, 1169, 1292, 1347, 1362, 1424, 1451, 1468, 1486, 1498, 1702, 2891, 2962, 3021; UV ($C_2H_5OH$) $\lambda_{max}$=206 ($\epsilon$=9299), 258 ($\epsilon$=214); Anal. Calcd. for $C_{13}H_{14}N_2O_2$: C,67.81; H,6.13; N,12.17; Found: C, 67.58; H. 6.26; N, 12.43; $^1H$ NMR (300 MHz, $CDC_{l3}$) $\delta$2.25–2.31 (m, 2H); 3.11 (t, J=6.5 Hz, 1H); 3.48–3.75 (m, 3H); 5.15 (s, 2H); 7.37 (s, 5H).

D. A solution of 5.3 g of benzyl 3-cyanopyrrolidine-1-carboxylate in 53 mL of anhydrous $CH_3OH$ saturated with HCl was stirred at room temperature for 36 hours and then quenched with the addition of 14.85 g of sodium bicarbonate. The reaction mixture was allowed to stand at refrigerator temperatures overnight and then concentrated in vacuo. The residue was triturated with THF and the salts removed by filtration. The solution was again concentrated in vacuo and chromatographed on silica gel (9/1 hexanes/ethyl acetate) to yield 4.36 g (72%) of benzyl 3-carbomethoxypyrrolidine-1-carboxylate as a clear oil. Rf=0.54 in 100% ethyl acetate; Mass Spectrum (FD+): M+1=263; IR (CHCl$_3$, cm$^{-1}$): 880, 1029, 1091, 1122, 1175, 1275, 1343, 1361, 1426, 1452, 1498, 1696, 1735, 2890, 2956, 3013, 3019, 3025; UV (C$_2$H$_5$OH): $\lambda_{max}$=205 ($\epsilon$=9796), 259 ($\epsilon$=191); $^1$H NMR (300 MHz,CDCl$_3$) $\delta$2.04–2.10 (m, 2H); 2.99–3.02 (m, 1H); 3.36–3.47 (m, 1H); 3.51–3.67 (m, 6H); 5.08 (s, 2H); 7.22–7.31 (m, 5H).

E. To a solution of 4.6 g of benzyl 3-carbomethoxypyrrolidine-1-carboxylate in 150 mL of anhydrous methanol was added 0.92 g of 10% Pd/C. The reaction mixture was placed under an atmosphere of hydrogen and stirred overnight at room temperature. The reaction mixture was then filtered through a Celite® pad, and the filtrate concentrated in vacuo. The residue was chromatographed on silica gel with 2–16% CH$_3$OH/CHCl$_3$ to give 1.40 g (62% yield) of 3-carbomethoxypyrrolidine as a clear oil. $^1$H NMR (300 MHz, CDCl$_3$) $\delta$1.90–2.10 (m, 2 H); 2.97–3.11 (m, 4H); 3.18–3.29 (m, 2H); 3.44 (s, 3H).

F. To a sample of 150 mg (0.47 mmol) of 5-[2-(2-amino-4-hydroxy-5,6,7,8-tetrahydropyrido[2,3-d]pyrimidin-6-yl)ethyl]thien-2-ylcarboxylic acid in a three-necked round bottomed flask under an atmosphere of nitrogen were added 3.6 mL anhydrous dimethylformamide and 0.11 mL (0.99 mmol) of N-methylmorpholine. The reaction mixture was stirred and 90 mg (0.51 mmol) of 2-chloro-4,6-dimethoxy-1,3,5-triazine were added at once. The reaction mixture was stirred at room temperature for 0.5 hours and 162 mg (1.25 mmol) of 3-carbomethoxypyrrolidine were added in 1.0 mL of dimethylformamide. After stirring at room temperature for another 3.5 hours, the reaction was concentrated in vacuo and the residue was chromatographed on silica gel with 2–8% CH$_3$OH/CHCl$_3$ to give 78 mg (40%) of methyl 1-{5-[2-(2-amino-4-hydroxy-5,6,7,8-tetrahydropyrido[2,3-d]pyrimidin-6-yl)ethyl]thien-2-ylcarbonyl}pyrrolidine-3-carboxylate as a white solid. Mass Spectrum (FAB+): M+1= 432; IR (KBr, cm$^{-1}$): 643, 734, 768, 809, 1219, 1336, 1417, 1464, 1601, 1684, 1736, 2854, 2924, 3390; UV (C$_2$H$_5$OH): $\lambda_{max}$=222 ($\epsilon$=21034), 279 ($\epsilon$=19777).

EXAMPLE 19 trans-Dimethyl 1-{5-[2-(2-amino-4-hydroxy-5,6,7,8-tetrahydropyrido[2,3-d]-pyrimidin-6-yl)-ethyl]thien-2-ylcarbonyl}pyrrolidine-2,4-dicarboxylate To a sample of 225 mg (0.70 mmol) of 5-[2-(2-amino-4-hydroxy-5,6,7,8-tetrahydropyrido[2,3-d]pyrimidin-6-yl)ethyl]thien-2-ylcarboxylic acid in a three-necked round bottomed flask under an atmosphere of nitrogen were added 3.5 mL anhydrous dimethylformamide and 0.08 mL (0.72 mmol) of N-methylmorpholine. The reaction mixture was stirred at room temperature and 135 mg (0.77 mmol) 2-chloro-4,6-dimethoxy-1,3,5-triazine were added at once. The reaction was stirred for 0.5 hours at room temperature, and 213 mg (1.14 mmol) of trans-dimethyl pyrrolidine-2,4-dicarboxylate were added in 1.0 mL of dimethylformamide. After stirring at room temperature for another 3.5 hours, the reaction was concentrated in vacuo and chromatographed on silica gel with 2–8% CH$_3$OH/CHCl$_3$ to give 185 mg (54%) of trans-dimethyl 1-{5-[2-(2-amino-4-hydroxy-5,6,7,8-tetrahydropyrido[2,3-d]pyrimidin-6-yl)-ethyl]thien-2-ylcarbonyl}pyrrolidine-2,4-dicarboxylate as a tan solid. Mass Spectrum (FAB+): M+1=490; $^1$H NMR (300 MHz, DMSO) $\delta$: 1.54–1.64 (m, 3H); 1.76–1.84 (m, 1H); 2.11–2.29 (m, 3H); 2.36–2.43 (m,--1H); 2.72–2.79 (m, 1H); 2.86–2.88 (m, 2H); 3.07–3.23 (m, 2H); 3.61 (s, 6H); 3.95–4.08 (m, 2H); 4.49–4.54 (M, 1H); 5.92 (s, 2H); 6.24 (d, J=1.6 Hz, 1H); 6.91–6.92 (m, 1H); 7.48 (d, J=2.4 Hz, 1H).

EXAMPLE 20

N-{5-[2-(2-amino-4-hydroxy-5,6,7,8-tetrahydropyrido[2,3-d]pyrimidin-6-yl)-ethyl]thien-2-ylsulfonyl}glycine To 1.065 g (4.1 mmol) of 2-bromothiophene-5-sulfonyl chloride, 1.1 mL of triethylamine, and a catalytic amount of dimethylaminopyridine in 10 mL of methylene chloride at room temperature was added 0.57 g (4.1 mmol) of ethyl glycinate hydrochloride. The resulting reaction mixture was then stirred at room temperature for 6 hours, diluted with water, and extracted with methylene chloride. The extracts were washed with brine, dried over sodium sulfate and concentrated in vacuo to 1.19 g of N-(5-bromothien-2-ylsulfonyl)glycine ethyl ester as a tan solid. $^1$H NMR (300 MHz, DMSO$_{d6}$) $\delta$: 1.13 (t, 3H), 3.75 (d, J=5 Hz, 2H), 4.01 (q, 2H), 7.31 (d, J=4 Hz, 1H), 7.42 (d, J=4 Hz, 1H), 8.58 (t, J=5 Hz, 1H).

A mixture of 436 mg (1.27 mmol) of 2-pivaloylamino-4-hydroxy-6-ethynylpyrido[2,3-d]pyrimidine, 415 mg of N-(5-bromothien-2-ylsulfonyl)glycine ethyl ester, 20 mg of palladium chloride, 54 mg of triphenylphosphine, 10 mg of cuprous iodide, and 0.4 mL of triethylamine in 7 mL of acetonitrile was heated to reflux under nitrogen for 1 hour. The resulting reaction mixture was then concentrated in vacuo and the residue flash chromatographed with 4% CH$_3$OH/chloroform to give 610 mg of N-[5-(2-pivaloylamino-4-hydroxypyrido[2,3-d]pyrimidin-6-ylethynyl)thien-2-ylsulfonyl]glycine ethyl ester as a tan solid. $^1$H NMR (300 MHz, DMSO-$_{d6}$) $\delta$1.13 (t, J=7 Hz, 3H), 1.25, (s, 9H), 3.79 (d, J=5.8 Hz, 2H), 3.99 (q, J=7 Hz, 2H), 7.48 (d, J=3.6 Hz, 1H), 7.56 (d, J=3.6 Hz, 1H), 8.51 (s, 1H), 8.65 (t, J=5.8 Hz, 1H), 8.99 (s, 1H).

To a mixture of 150 mg of N-[5-(2-pivaloylamino-4-hydroxypyrido[2,3-d]pyrimidin-6-ylethynyl)thien-2-ylsulfonyl]glycine ethyl ester in 25 mL of glacial acetic acid was added 100 mg of platinum oxide. This mixture was stirred under hydrogen for 24 hours and an additional 100 mg of platinum oxide was added. The hydrogenation was resumed for another 24 hours and the reaction mixture was then filtered through Celite® and the filtrate concentrated in vacuo. The residue was flash chromatographed on silica gel using 3.5% CH$_3$OH and chloroform to give 48 mg of N-{5-[2-(2-pivaloylamino-4-hydroxy-5,6,7,8-tetrahydropyrido[2,3-d]pyrimidin-6-yl)-ethyl]thien-2-ylsulfonyl}glycine ethyl ester as a white solid. $^1$H NMR (300 MHz, DMSO-$_{d6}$, $\delta$1.10 (t, J=7 Hz, 3H), 1.17 (s, 9H), 1.62 (m, 3H), 1.90 (m, 1H), 2.52 (m, 1H), 2.91 (m, 3H), 3.25 (m, 1H), 3.68 (d, J=4.9 Hz, 2H), 3.97 (q, J=7 Hz, 2H), 6.45 (s, 1H), 6.92 (d, J=3.5 Hz, 1H, 7.38 (d, J=3.5 Hz, 1H), 8.31 (t, J=4.9 Hz, 1H).

A solution of 33 mg (0.062 mmol) of N-{5-[2-(2-pivaloylamino-4-hydroxy-5,6,7,8-tetrahydropyrido[2,3-d]pyrimidin-6-yl)-ethyl]thien-2-ylsulfonyl}glycine ethyl ester in 3.0 mL of 1.0N sodium hydroxide was stirred at room temperature for 24 hours. The reaction mixture was then acidified with 1.0N hydrochloric acid and the white precipitate was collected by filtration to give 28 mg of N-{5-[2-(2-amino-4-hydroxy-5,6,7,8-tetrahydropyrido[2,3-d]pyrimidin-6-yl)-ethyl]thien-2-ylsulfonyl}glycine.

EXAMPLE 21

Hard gelatin capsules containing a compound of Formula I ("active ingredient") are prepared using the following ingredients:

| Quantity | (mg/capsule) |
|---|---|
| Starch, dried | 200 |
| Magnesium stearate | 10 |
| Active ingredient | 250 |
| Total | 460 |

EXAMPLE 22

A tablet containing a compound of Formula I is prepared using the ingredients below:

| Quantity | (mg/capsule) |
|---|---|
| Active ingredient | 250 |
| Cellulose, microcrystalline | 400 |
| Silicon dioxide, fumed | 10 |
| Stearic acid | 5 |
| Total | 665 |

The components are blended and compressed to form tablets each weighing 665 mg.

EXAMPLE 23

An aerosol solution containing a compound of Formula I is prepared containing the following components:

|  | Percent |
|---|---|
| Active ingredient | 0.25 |
| Ethanol | 25.75 |
| Propellant (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 24

Tablets, each containing 60 mg of a compound of Formula I, are prepared as follows:

|  | Quantity (mg/tablet) |
|---|---|
| Active ingredient | 60 |
| Starch | 45 |
| microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, then are added to the granules which, after mixing, are compressed on a tablet machine to yield tablets each weighing 150 mg.

EXAMPLE 25

Capsules, each containing 80 mg of a compound of Formula I, are made as follows:

|  | Quantity (mg/capsule) |
|---|---|
| Active ingredient | 80 |
| Starch | 59 |
| microcrystalline celluose | 59 |
| Magnesium stearate | 2 |
| Total | 200 |

The active ingredient, cellulose, starch, and magnesium stearate are blended, passed through a No. 45 mesh U.S. sieve, and filled into hard gelatin capsules in 200 mg quantities.

EXAMPLE 26

Suppositories, each containing 225 mg of a compound of Formula I, are made as follows:

|  | Quantity (mg/unit) |
|---|---|
| Active ingredient | 225 |
| Saturated fatty acid glycerides | 2,000 |
| Total | 2,225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 27

Suspensions, each containing 50 mg of a compound of Formula I per 5 mL dose, are made as follows:

|  | Quantity |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

EXAMPLE 28

An intravenous formulation containing a compound of Formula I can be prepared as follows:

|  | Quantity |
|---|---|
| Active ingredient | 100 mg |
| Isotonic saline | 1000 mL |

EXAMPLE 29

N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-aspartic acid was evaluated against 6C3HED lymphosarcoma tumor in C3H female mice with the compound given daily, IV bolus injection, for 8 days. Compounds were administered in units of mg/kg of body weight. At the end of treatment, tumor weight was estimated using an electronic caliper interfaced to a microcomputer, and average tumor weight was calculated for each dosing level and a control group. Percentage inhibition of tumor growth was calculated as % inhibition of tumor growth according to the expression:

[1−(average tumor weight experimental group/average tumor weight control group)]×100.

Percentage inhibition was not calculated at a particular dosing level if mortality exceeded 20%. Cumulative dose was calculated by multiplying the daily dose by the number of days doses were administered.

N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-aspartic acid showed 100% inhibition at both 200 and 100 mg/kg.

EXAMPLE 30

The Ki inhibition constant (nanomoles) against human monofunctional GARFT for N-(N-{5-[2-(2-amino-4-hydroxy-5,6,7,8-tetrahydropyrido[2,3-d]pyrimidin-6-yl)-ethyl]thien-2-ylcarbonyl}-L-γ-glutamyl)-D-aspartic acid is 0.244 nM; for N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-glutamic acid 1-tert.-butyl-2,2-diethyl ester the Ki is 7.7 nM; for N-{5-[2-(2-amino-4-hydroxy-5,6,7,8-tetrahydropyrido[2,3-d]pyrimidin-6-yl)-ethyl]thien-2-ylcarbonyl}-L-homocysteic acid α-methyl ester, the Ki is 3.5 nM; and for 2-{5-[2-(2-amino-4-hydroxy-5,6,7,8-tetrahydropyrido[2,3-d]pyrimidin-6-yl)ethyl]thien-2-ylcarbonylamino}-3-(2H-tetrazol-5-yl)propanoic acid diammonium salt the Ki is 155.8 nM [See: Henderson, *Biochem, J.*, 127: 321–333, (1972) for linear equation of steady-state kinetics of enzymes and subcellular particles interacting with tightly bound inhibitors].

EXAMPLE 31

Folate binding protein derived from human KB cells [See Habeck, *Cancer Research*, 54: 1021–1026, (1994)] for N-(N-{5-[2-(2-amino-4-hydroxy-5,6,7,8-tetrahydropyrido[2,3-d]pyrimidin-6-yl)-ethyl]thien-2-ylcarbonyl}-L-γ-glutamyl)-D-aspartic acid is 0.387 and for N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-glutamic acid 1-tert.-butyl-2,2-diethyl ester it is 2.238.

EXAMPLE 32

The $IC_{50}$, that is the concentration inhibiting cell growth of a CCRF-CEM cell line by 50% as compared to control measured in micrograms, for N-(N-{4-[2-(2-amino-4-hydroxy-5,6,7,8-tetrahydropyrido[2,3-d]pyrimidin-6-yl)ethyl]benzoyl}-L-γ-glutamyl)-D-aspartic acid is 1.6 µg/mL. For N-(N-{5-[2-(2-amino-4-hydroxy-5,6,7,8-tetrahydropyrido[2,3-d]pyrimidin-6-yl)-ethyl]thien-2-ylcarbonyl}-L-γ-glutamyl)-D-aspartic acid, the $IC_{50}$ is 0.100 µg/mL. For N-(N-{5-[2-(2-amino-4-hydroxy-5,6,7,8-tetrahydropyrido[2,3-d]pyrimidin-6-yl)ethyl]thien-2-ylcarbonyl}-L-γ-glutamyl)-D-glutamic acid 1-tert.-butyl-2,2-diethyl ester, the $IC_{50}$ is 1.0 µg/mL. For N-{5-[2-(2-amino-4-hydroxy-5,6,7,8-tetrahydropyrido[2,3-d]pyrimidin-6-yl)-ethyl]thien-2-ylcarbonyl}-L-homocysteic acid α-methyl ester, the $IC_{50}$ is 0.200 µg/mL. For N-{5-[2-(2-amino-4-hydroxy-5,6,7,8-tetrahydropyrido[2,3-d]pyrimidin-6-yl)-ethyl]thien-2-ylcarbonyl}-L-homocysteic acid, the $IC_{50}$ is 0.82 µg/mL. For 2-{4-[2-(2-amino-4-hydroxy-5,6,7,8-tetrahydropyrido[2,3-d]pyrimidin-6-yl)ethyl]benzoylamino}-3-(2H-tetrazol-5-yl)propanoic acid diammonium salt, the $IC_{50}$ is 28.6 µg/mL. For 2-{5-[2-(2-amino-4-hydroxy-5,6,7,8-tetrahydropyrido[2,3-d]pyrimidin-6-yl)ethyl]thien-2-ylcarbonylamino}-3-(2H-tetrazol-5-yl)propanoic acid diammonium salt the $IC_{50}$ is >100 µg/mL.

What is claimed is:

1. A compound of the formula:

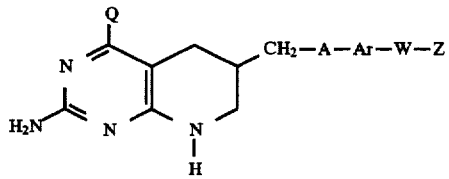

in which:

Q is —OH or —NH$_2$;

A is —CH$_2$—, —CH$_2$CH$_2$—, —O—, or —S—;

—Ar— is a divalent aromatic ring;

W is —CO— or —SO$_2$—; and

Z is:

(A) an α-amino acid group of the formula

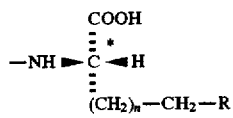

wherein * designates a chiral center in the L configuration.
n has a value of from 0 to 4, and
R is:
(i) V, wherein V is a tetrazolyl group of the formula

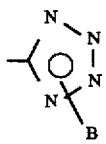

where B is hydrogen, $C_1$–$C_4$ alkyl, or $C_1$–$C_4$ hydroxyalkyl, or (ii) —$SO_3H$;

(B) a tetrazolyl group of the formula

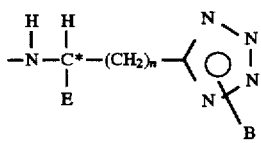

wherein n has a value of from 0 to 4 and E is —COOH or V, wherein V is a tetrazolyl group as defined herein and, if n is greater than 0 or E is other than V, the carbon atom designated * is in the L configuration;

(C) —$NHR^1$, where $R^1$ is hydrogen or a substituted or unsubstituted $C_1$–$C_4$ alkyl, $C_1$–$C_4$ hydroxyalkyl, cycloalkyl, or polycycloalkyl group;

(D) —$NR^2R^3$ where $R^2$ and $R^3$ are independently $C_1$–$C_4$ alkyl, $C_1$–$C_4$ hydroxyalkyl or COOT, where T is hydrogen or $C_1$–$C_4$ alkyl;

(E)

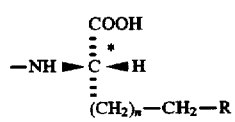

where each T is independently as defined previously, n has a value of from 0 to 4, and y has a value of 0 or 1;

(F)

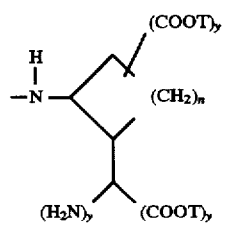

where n, T and y are as defined herein, provided at least one y is other than zero;

(G)

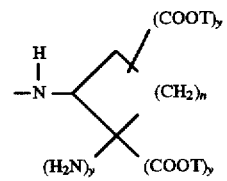

where n, T and y are as defined herein, provided at least one y is other than zero; or (H) —NHOH;

and the pharmaceutically acceptable salts and esters thereof.

2. A compound according to claim 1 which is 1,3-bis-(tetrazol-5-yl)-1-{4-[2-(2-amino-4-hydroxy-5,6,7,8-tetrahydropyrido[2,3d]pyrimidin-6-yl)ethyl]benzoylamino}-propane.

3. A compound according to claim 1 which is 2-{4-[2-(2-amino-4-hydroxy-5,6,7,8-tetrahydropyrido[2,3-d]pyrimidin-6-yl)ethyl]benzoylamino}bicyclo[2.2.1]heptane-2-carboxylic acid.

4. A compound according to claim 1 which is 1-{5-[2-(2-amino-4-hydroxy-5,6,7,8-tetrahydropyrido[2,3-d]pyrimidin-6-yl)ethyl]thien-2-ylcarbonylamino}cyclohexane-1-carboxylic acid.

5. A compound according to claim 1 which is 1-{5-[2-(2-amino-4-hydroxy-5,6,7,8-tetrahydropyrido[2,3-d]pyrimidin-6-yl)ethyl]thien-2-ylcarbonylamino}cyclopropane-1-carboxylic acid.

6. A compound according to claim 1 which is 1-{5-[2-(2-amino-4-hydroxy-5,6,7,8-tetrahydropyrido[2,3-d]pyrimidin-6-yl)ethyl]thien-2-ylcarbonylamino}cyclopentane-1-carboxylic acid.

7. A compound of the formula:

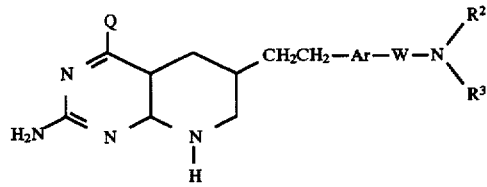

in which
Ar is phenylene or thienediyl;
W is —CO— or —$SO_2$—;
Q is hydroxy or amino;
(a) $R^2$ and $R^3$ when taken together with the nitrogen atom to which they are attached are a pyrrolidino or piperidino group substituted with one or two groups of the formula COOT in which T is hydrogen or alkyl of 1 to 4 carbon atoms, or
(b) when taken separately, $R^2$ is hydrogen and $R^3$ is:
(1) hydroxy,
(2) cycloalkyl of 3 to 8 carbon atoms substituted with —COOT in which T is hydrogen or alkyl of 1 to 4 carbon atoms, or (3) 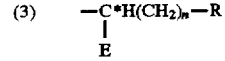

in which
E is hydrogen, carboxy, or tetrazolyl and if E is other than hydrogen the configuration about the carbon atom designated * is L, n has a value of 0 to 4, and R is
(i) tetrazolyl,
(ii) —SO₃H,
(iii) glycyl, or
(iv) —CO—J in which J is an α-amino acid residue of the D-configuration, or provided E is not carboxy, J is hydroxy or alkoxy of 1 to 4 carbon atoms.

8. A compound according to claim 5 in which Q is hydroxy, W is —CO—, and R² and R³ when taken together with the nitrogen atom to which they are attached are a pyrrolidino or piperidino group substituted with one or two groups of the formula COOT in which T is hydrogen or alkyl of 1 to 4 carbon atoms.

21. A method of inhibiting the activity of GARFT in a mammal which comprises administering thereto an effective amount of a compound according to claim 1.

22. A method of treating susceptible neoplasms in a mammal which comprises administering thereto an effective amount of a compound according to claim 1.

23. A method of treating psoriasis in a mammal which comprises administering thereto an effective amount of a compound according to claim 1.

24. A method of treating arthritis in a mammal which comprises administering thereto an effective amount of a compound according to claim 1.

25. A compound of the formula:

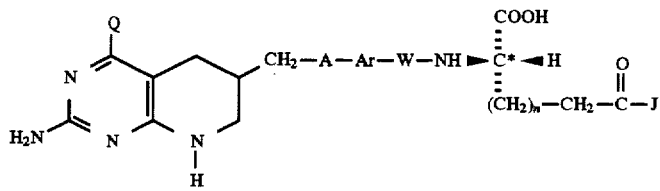

9. A compound according to claim 8 which is methyl 1-{5-[2-(2-amino-4-hydroxy-5,6,7,8-tetrahydropyrido[2,3-d]pyrimidin-6-yl)ethyl]thien-2-ylcarbonyl}pyrrolidine-3-carboxylate.

10. A compound according to claim 8 which is trans-dimethyl 1-{5-[2-(2-amino-4-hydroxy-5,6,7,8-tetrahydropyrido[2,3-d]pyrimidin-6-yl)-ethyl]thien-2-ylcarbonyl}pyrrolidine-2,4-dicarboxylate.

11. A compound according to claim 7 in which Q is hydroxy, W is —CO—, R² is hydrogen, and R³ is hydroxy.

12. A compound according to claim 11 which is N-{5-[2-(2-amino-4-hydroxy-5,6,7,8-tetrahydropyrido[2,3-d]pyrimidin-6-yl)ethyl]thien-2-ylcarbonyl}hydroxylamine.

13. A compound according to claim 7 in which Q is hydroxy, W is —CO—, R² is hydrogen, and R³ is cycloalkyl of 3 to 8 carbon atoms substituted with —COOT in which T is hydrogen or alkyl of 1 to 4 carbon atoms.

14. A compound according to claim 7 in which Q is hydroxy, W is —CO—, R² is hydrogen, and R³ is —CH(E)(CH₂)ₙ—R in which E is hydrogen, carboxy, or tetrazolyl, n has a value of 0 to 4, and R is tetrazolyl or —SO₃H.

15. A compound according to claim 14 which is N-{5-[2-(2-amino-4-hydroxy-5,6,7,8-tetrahydropyrido[2,3-d]pyrimidin-6-yl)-ethyl]thien-2-ylsulfonyl}glycine.

16. A compound according to claim 7 in which Q is hydroxy, W is —CO—, R² is hydrogen, and R³ is —CH(E)(CH₂)ₙ—R in which E is hydrogen or tetrazolyl, n has a value of 0 to 4, and R is —CO—J in which J is hydroxy or alkoxy of 1 to 4 carbon atoms.

17. A compound according to claim 16 which is 2-{4-[2-(2-amino-4-hydroxy-5,6,7,8-tetrahydropyrido[2,3-d]pyrimidin-6-yl)ethyl]benzoylamino}-3-(2H-tetrazol-5-yl)propanoic acid.

18. A compound according to claim 16 which is 2-{5-[2-(2-amino-4-hydroxy-5,6,7,8-tetrahydropyrido[2,3-d]pyrimidin-6-yl)ethyl]thien-2-ylcarbonylamino}-3-(2H-tetrazol-5-yl)propanoic acid.

19. A compound according to claim 7 which is N-{5-[2-(2-amino-4-hydroxy-5,6,7,8-tetrahydropyrido[2,3-d]pyrimidin-6-yl)ethyl]thien-2-ylcarbonyl}glycine ethyl ester.

20. A pharmaceutical composition comprising a compound according to claim 1 in combination with a pharmaceutically acceptable carrier.

in which:

Q is —OH or —NH₂;

A is —CH₂—, —CH₂CH₂—, —O—, or —S—;

—Ar— is a divalent aromatic ring;

W is —CO— or —SO₂—;

n has a value of from 0 to 4,

* designates a chiral center in the L configuration; and

J is an amino acid residue of glucine, D-aspartic acid, D-proline, or D-homogysteic acid which residue is linked through the α-amino group.

26. A compound according to claim 25 in which

A is —CH₂—,

—Ar— is phenylene or thienediyl;

W is —CO—;

n has a value of 2, and

J is D-aspartic acid linked through its α-amino group.

27. A compound according to claim 26 which is N-(N-{4-[2-(2-amino-4-hydroxy-5,6,7,8-tetrahydropyrido[2,3-d]pyrimidin-6-yl)ethyl]benzoyl}-L-γ-glutamyl)-D-aspartic acid.

28. A compound according to claim 26 which is N-(N-{5-[2-(2-amino-4-hydroxy-5,6,7,8-tetrahydropyrido[2,3-d]pyrimidin-6-yl)-ethyl]thien-2-ylcarbonyl}-L-γ-glutamyl)-D-aspartic acid.

29. A compound of the formula:

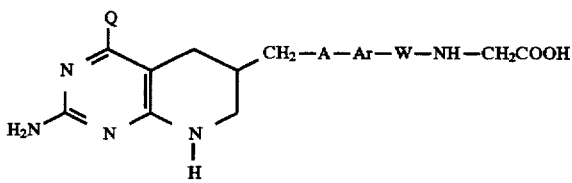

in which:

Q is —OH or —NH₂;

A is —CH₂—, —CH₂CH₂—, —O—, or —S—;

—Ar— is a divalent aromatic ring; and

W is —CO— or —SO₂—.

30. A compound according to claim 29 in which Q is hydroxy, and W is —CO—.

31. A compound according to claim 30 which is N-{5-[2-(2-amino-4-hydroxy-5,6,7,8-tetrahydropyrido[2,3-d]pyrimidin-6-yl)-ethyl]thien-2-ylcarbonyl}glycine.

32. A compound selected from the group consisting of N-(N-{5-[2-(2-amino-4-hydroxy-5,6,7,8-tetrahydropyrido[2,3-d]pyrimidin-6-yl)ethyl]thien-2-ylcarbonyl}-γ-L-glutamyl)-D-glutamate tris-(tert.-butyl) ester, N-{5-[2-(2-amino-4-hydroxy-5,6,7,8-tetrahydropyrido[2,3-d]pyrimidin-6-yl)-ethyl]thien-2-ylcarbonyl}-L-homocysteic acid α-methyl ester, and N-{5-[2-(2-amino-4-hydroxy-5,6,7,8-tetrahydropyrido[2,3-d]pyrimidin-6-yl)ethyl]thien-2-ylcarbonyl}-L-homocysteic acid.

* * * * *

UNITED STATES PATENT AND TRADEMARK OFFICE
CERTIFICATE OF CORRECTION

PATENT NO.    : 5,786,358
DATED         : JULY 28, 1998
INVENTOR(S)   : CHUAN SHIH ET AL.

It is certified that error appears in the above-identified patent and that said Letters Patent is hereby corrected as shown below:

On the Title Page: Line [73], change "Assignee: The Trustees of Princeton University, Princeton, N.J." to -- "Assignee: The Trustees of Princeton University, Princeton, N.J. and Eli Lilly & Co., Indianapolis, IN".

Signed and Sealed this

Fourteenth Day of March, 2000

*Attest:*

Q. TODD DICKINSON

*Attesting Officer*        Commissioner of Patents and Trademarks